(12) United States Patent
Saitoh et al.

(10) Patent No.: US 7,129,386 B2
(45) Date of Patent: Oct. 31, 2006

(54) SUBSTITUTED ANTHRYL DERIVATIVE AND ELECTROLUMINESCENCE DEVICE USING THE SAME

(75) Inventors: Akihito Saitoh, Kanagawa (JP); Akihiro Senoo, Kanagawa (JP); Kazunori Ueno, Kanagawa (JP); Keiji Okinaka, Kanagawa (JP); Koichi Suzuki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/875,244

(22) Filed: Jun. 25, 2004

(65) Prior Publication Data

US 2005/0099115 A1 May 12, 2005

(30) Foreign Application Priority Data

Jun. 27, 2003 (JP) ............................. 2003-184264

(51) Int. Cl.
C07C 15/28 (2006.01)
H01J 1/62 (2006.01)
C07C 211/00 (2006.01)
C07F 7/08 (2006.01)

(52) U.S. Cl. ................. 585/26; 564/427; 556/489; 428/690; 428/917; 313/504; 313/506; 257/102; 257/103

(58) Field of Classification Search ................ 313/504, 313/506; 257/102, 103; 428/690, 917; 585/26; 556/489; 564/427
See application file for complete search history.

(56) References Cited

U.S. PATENT DOCUMENTS

| | | | |
|---|---|---|---|
| 4,539,507 A | 9/1985 | Van Slyke et al. | 313/504 |
| 4,720,432 A | 1/1988 | Van Slyke et al. | 428/457 |
| 4,885,211 A | 12/1989 | Tang et al. | 428/457 |
| 5,130,603 A | 7/1992 | Tokailin et al. | 313/504 |
| 5,151,629 A | 9/1992 | Van Slyke | 313/504 |
| 5,227,252 A | 7/1993 | Murayama et al. | 428/690 |
| 5,247,190 A | 9/1993 | Friend et al. | 257/40 |
| 5,317,169 A | 5/1994 | Nakano et al. | 257/40 |
| 5,382,477 A | 1/1995 | Saito et al. | 428/690 |
| 5,409,783 A | 4/1995 | Tang et al. | 428/690 |
| 5,514,878 A | 5/1996 | Holmes et al. | 257/40 |
| 5,635,308 A | 6/1997 | Inoue et al. | 428/690 |
| 5,672,678 A | 9/1997 | Holmes et al. | 528/373 |
| 5,726,457 A | 3/1998 | Nakano et al. | 257/40 |
| 5,759,444 A | 6/1998 | Enokida et al. | 252/301.16 |
| 6,093,864 A | 7/2000 | Tokailin et al. | 585/25 |
| 6,713,192 B1 | 3/2004 | Fukuoka et al. | 428/690 |
| 6,830,829 B1* | 12/2004 | Suzuki et al. | 428/690 |
| 6,929,870 B1* | 8/2005 | Ishida et al. | 428/690 |
| 2002/0048688 A1 | 4/2002 | Fukuoka et al. | 428/690 |
| 2002/0177009 A1 | 11/2002 | Suzuki et al. | 428/690 |
| 2002/0192497 A1* | 12/2002 | Wang et al. | 428/690 |
| 2004/0263067 A1* | 12/2004 | Saitoh et al. | 313/504 |
| 2004/0265632 A1* | 12/2004 | Okinaka et al. | 428/690 |
| 2006/0014046 A1* | 1/2006 | Wang et al. | 428/690 |

FOREIGN PATENT DOCUMENTS

| | | |
|---|---|---|
| EP | 0 952 200 A2 | 10/1999 |
| JP | 2-247278 | 10/1990 |
| JP | 2-282262 | 11/1990 |
| JP | 3-255190 | 11/1991 |
| JP | 4-145192 | 5/1992 |
| JP | 5-202356 | 8/1993 |
| JP | 5-247460 | 9/1993 |
| JP | 8-12600 | 1/1996 |
| JP | 9-157643 | 6/1997 |
| JP | 9-202878 | 8/1997 |
| JP | 9-227576 | 9/1997 |
| JP | 10-72579 | 3/1998 |
| JP | 11-8068 | 1/1999 |
| JP | 11-111460 | 4/1999 |
| JP | 2000-273056 | 10/2000 |
| JP | 2001-284050 | 10/2001 |

OTHER PUBLICATIONS

Hideyuki Tukada, J.Chem. Soc., Chem. Commun., vol. 19, pp. 2293-2294 (1994).*

(Continued)

*Primary Examiner*—Porfirio Nazario-Gonzalez
(74) *Attorney, Agent, or Firm*—Fitzpatrick, Cella, Harper & Scinto

(57) ABSTRACT

There is disclosed a substituted anthryl derivative is represented by the following general formula (1). The use of the substituted anthryl derivative allows the production of an organic electroluminescence device showing an extremely pure luminescence hue, and an optical output with high luminous efficiency, high luminance, and long life

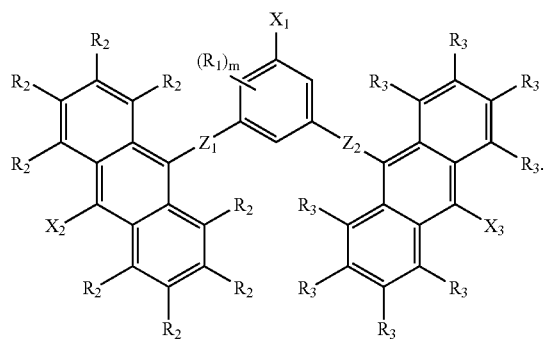

(1)

1 Claim, 2 Drawing Sheets

OTHER PUBLICATIONS

Burroughs et al., "Light-Emitting Diodes Based on Conjugated Polymers", *Nature*, vol. 347, Oct. 11, 1990, pp. 539-541.

Tang et al., "Organic Electroluminescent Diodes", *Appl. Phys. Lett.*, vol. 51, No. 12, Sep. 21, 1987, pp. 913-915.

Baldo et al., "Very High-Efficiency Green Organic Light-Emitting Devices Based on Electrophosphorescence", *Appl. Phys. Lett.*, vol. 75, No. 1, Jul. 5, 1999, pp. 4-6.

* cited by examiner

SUBSTITUTED ANTHRYL DERIVATIVE AND ELECTROLUMINESCENCE DEVICE USING THE SAME

BACKGROUND OF THE INVENTION

1. Field of the Invention

The present invention relates to an organic electroluminescence device, and more particularly, to a device from which light is emitted by applying an electric field on a thin film made of an organic compound.

2. Related Background Art

An organic electroluminescence device (hereinafter, simply referred to as an organic EL device) is a device that includes a thin film made of a fluorescence compound between an anode and a cathode, generates an exciton from the fluorescence compound by injection of an electron and an electron hole (hereinafter, also simply referred to as a hole) from each electrode, and uses light to be radiated when the exciton returns to the ground state.

The study conducted by Eastman Kodak Company in 1987 (Tang and SA Van Slyke, Appl. Phys. Lett., 51, p. 913, (1987)) reported light emission at about 1,000 cd/m$^2$ by an applied voltage of about 10 V from a device including a function-separated two-layer structure having an anode made of ITO and a cathode made of magnesium-silver alloy where an aluminum quinolinol complex is used as each of an electron-transporting material and a light-emitting material and a triphenylamine derivative is used as a hole-transporting material. In this case, related patent documents include U.S. Pat. Nos. 4,539,507, 4,720,432, and 4,885,211.

In addition, light emission at spectra ranging from ultra-violet through infra-red can be allowed by changing the type of a fluorescence organic material. Recently, various compounds have been studied actively and described in many publications such as U.S. Pat. Nos. 5,151,629, 5,409,783, and 5,382,477, Japanese Patent Application Laid-Open Nos. H02-247278, H03-255190, H05-202356, H09-202878 and H09-2275756.

Furthermore, in addition to the organic EL devices using low molecular weight materials as described above, an organic EL device using a conjugated polymer has been reported from the group of the Cambridge University (Nature, 347, 539 (1990)). This report has confirmed light emission from a monolayer by film formation with polyphenylene vinylene (PPV) in a coating system. Patents related to an organic EL device using a conjugated polymer include U.S. Pat. Nos. 5,247,190, 5,514,878, and 5,672,678, Japanese Patent Application Laid-Open Nos. H04-145192 and H05-247460.

Recently, furthermore, an organic phosphorescence device using an iridium complex such as Ir (ppy)$_3$ (Appl. Phys. Lett., 75, 4 (1999)) has been attracting attention and high luminous efficiency thereof has been reported.

Recent advances in organic EL devices are remarkable and the characteristics thereof allow the formation of light-emitting devices having high luminance with a low applied voltage, the variety of emission wavelengths, high-speed responsiveness, low profile, and lightweight, suggesting the possibility for extensive uses. However, organic EL devices still involve many problems in durability, such as chronological changes by prolonged use, and degradation with atmospheric gases containing oxygen, humidity, or the like. When applications of organic EL devices to full-color displays and so on are taken into consideration, under the present circumstances, blue-, green-, and red light-emissions with extended-life, high conversion rate, and high color purity have been demanded.

Examples of the materials and organic EL devices containing anthracene rings include a phenyl anthracene derivative disclosed in Japanese Patent Application Laid-Open No. H08-012600. In particular, when a phenyl anthracene derivative was used as a blue light-emitting material or an electron-injection transporting material, the phenyl anthracene derivative was believed to allow the formation of a good organic film because of its low crystallinity. However, the luminous efficiency and useful life of the phenyl anthracene ring were insufficient in practical application.

An aminoanthracene derivative and a diaminoanthracene derivative have been disclosed as other examples in Japanese Patent Application Laid-Open Nos. H09-157643 and H10-072579, respectively. In the documents, those materials were believed to generate green light-emission when they were used as light-emitting materials. However, devices prepared from those materials showed insufficient luminous efficiencies and their useful lives were still insufficient in practical application.

Japanese Patent No. 3008897 disclosed as another example a device using a particular bianthryl compound as a light-emitting material, which was believed to attain light emission with high luminance. However, the publication describes nothing about luminous efficiency and useful life.

Japanese Patent Application Laid-Open No. H11-008068 disclosed as still another example a device using a particular anthracene compound having an olefin portion as a light-emitting material, which was believed to attain light emission from yellow to red. However, the device showed insufficient luminous efficiency in practical application.

Furthermore, Japanese Patent Application Laid-Open No. 2001-284050 disclosed as another example a device that contains an anthracene derivative having a particular structure, an electron-transporting compound, and another fluorescence compound in a light-emitting medium layer. This device was believed to provide a red light-emitting device with improved reliability. However, the device showed insufficient luminous efficiency in practical application. In addition, it was difficult to obtain blue light emission because of its device configuration.

SUMMARY OF THE INVENTION

The present invention has been achieved for solving the disadvantages of the prior art as described above and intends to provide an organic EL device having an optical output with extremely pure luminescence hue, high luminous efficiency, high luminance, and long life. Furthermore, the present invention intends to provide an organic EL device that can be easily manufactured and comparatively cheap.

The inventors of the present invention have made extensive study to solve the above problems, thereby completing the present invention.

That is, the present invention provides a substituted anthryl derivative represented by the following general formula (1):

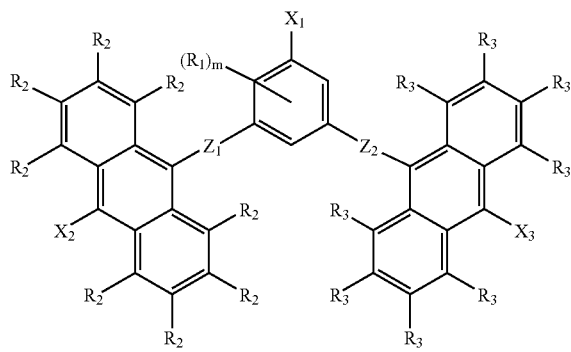

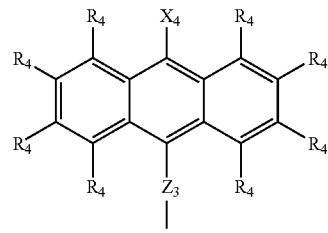

(Wherein $X_1$ is one selected from the group consisting of a hydrogen atom, a heavy hydrogen atom, a halogen atom, a substituted or unsubstituted alkyl group, aralkyl group, amino group, alkoxy group, sulfide group, aryl group, and heterocyclic group, and $X_1$ may be the same or different;

each of $X_2$ and $X_3$ is one selected from the group consisting of a heavy hydrogen atom, a substituted or unsubstituted alkyl group, alkenyl group, alkynyl group, aralkyl group, alkoxy group, and sulfide group, aryl groups including a substituted phenyl group, a substituted or unsubstituted terphenyl group, naphthyl group, phenanthryl group, pyrenyl group, tetracenyl group, and perylenyl group, a substituted or unsubstituted heterocyclic group, and a substituted silyl group, $X_2$ and $X_3$ may be the same or different, and, when $X_1$ is not an aryl group having an amino group, one of $X_2$ and $X_3$ may be a substituted or unsubstituted amino group, or a substituted or unsubstituted amino group having a coupling group;

each of $Z_1$ and $Z_2$ is one selected from the group consisting of a direct bond, a substituted or unsubstituted alkylene group, alkenylene group, alkynylene group, aralkylene group, arylene group, and divalent heterocyclic group, and a divalent substitutent having a coupling group, and $Z_1$ and $Z_2$ may be the same or different;

$R_1$ is one selected from the group consisting of a hydrogen atom, a heavy hydrogen atom, a halogen atom, a substituted or unsubstituted alkyl group, and alkoxy group, and $R_1$ may be the same or different;

each of $R_2$ and $R_3$ is one selected from the group consisting of a hydrogen atom, a heavy hydrogen atom, a halogen atom, a substituted or unsubstituted alkyl group, aryl group, alkoxy group, and amino group, and $R_2$ and $R_3$ may be the same or different; and m is an integer of 0 to 3.).

Furthermore, the present invention provides a substituted anthryl derivative, in which $X_1$ is represented by the following general formula (2):

(Wherein $X_4$ is one selected from the group consisting of a hydrogen atom, a heavy hydrogen atom, a halogen atom, a substituted or unsubstituted alkyl group, alkenyl group, alkynyl group, aralkyl group, alkoxy group, and sulfide group, an amino group, an aryl group, a heterocyclic group, and a substituted silyl group, and $X_4$ may be the same or different;

$Z_3$ is one selected from the group consisting of a direct bond, a substituted or unsubstituted alkylene group, alkenylene group, alkynylene group, aralkylene group, arylene group, and divalent heterocyclic group, and a divalent substituent having a coupling group; and $R_4$ is one selected from the group consisting of a hydrogen atom, a heavy hydrogen atom, a halogen atom, a substituted or unsubstituted alkyl group, aryl group, alkoxy group, and amino group, and $R_4$ may be the same or different.).

Furthermore, the present invention provides a substituted anthryl derivative, in which $X_1$ is represented by the following general formula (3):

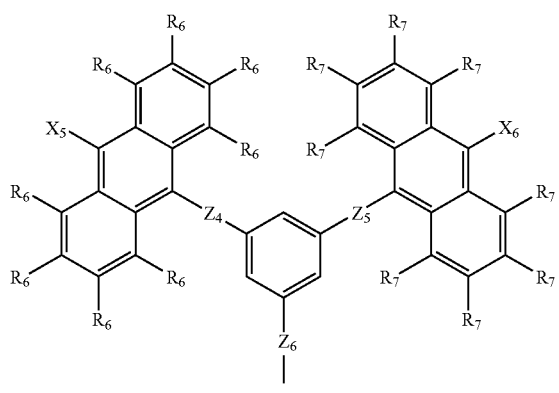

(Wherein each of $X_5$ and $X_6$ is one selected from the group consisting of a heavy hydrogen atom, a halogen atom, a substituted or unsubstituted alkyl group, alkenyl group, alkynyl group, aralkyl group, alkoxy group, and sulfide group, aryl groups including a substituted phenyl group, substituted or unsubstituted biphenyl group, terphenyl group, naphthyl group, phenanthryl group, pyrenyl group, tetracenyl group, and perylenyl group, a substituted or unsubstituted heterocyclic group, and a substituted silyl group, and $X_5$ and $X_6$ may be the same or different;

each of $Z_4$ and $Z_5$ is one selected from the group consisting of a direct bond, a substituted or unsubstituted alkylene group, alkenylene group, alkynylene group, aralkylene group, arylene group, and divalent heterocyclic group, and a divalent substituent having a coupling group, and $Z_4$ and $Z_5$ may be the same or different;

$Z_6$ is one selected from the group consisting of a direct bond, a substituted or unsubstituted alkylene group, alkenylene group, alkynylene group, and aralkylene group, arylene groups including a substituted or unsubstituted phenylene group, biphenylene group, terphenylene group, naphthylene group, fluorenylene group, phenanthrylene group, pyrenylene group, tetracenylene group, pentacenylene group, and perylenylene group, a substituted or unsubstituted divalent heterocyclic group, and a divalent substitutent having a coupling group, and $Z_6$ may be the same or different;

each of $R_6$ and $R_7$ is one selected from the group consisting of a hydrogen atom, a heavy hydrogen atom, a halogen atom, a substituted or unsubstituted alkyl group, aryl group, alkoxy group, and amino group, and $R_6$ and $R_7$ may be the same or different; and n is an integer of 0 to 3.).

DETAILED DESCRIPTION OF THE PREFFERED EMBODIMETS

Figure 1:
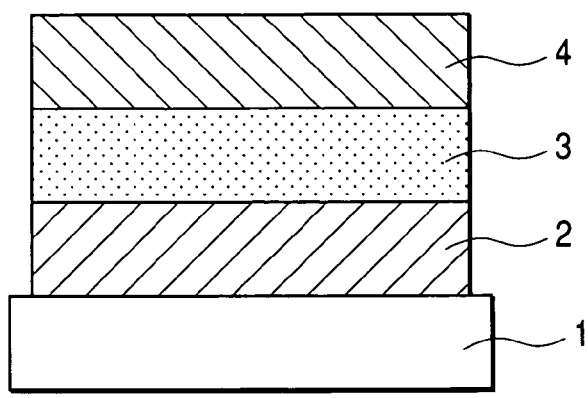
FIG. 1 is a cross sectional diagram illustrating an embodiment of an organic EL device of the present invention.

The present invention provides a substituted anthryl derivative represented by the following general formula (1):

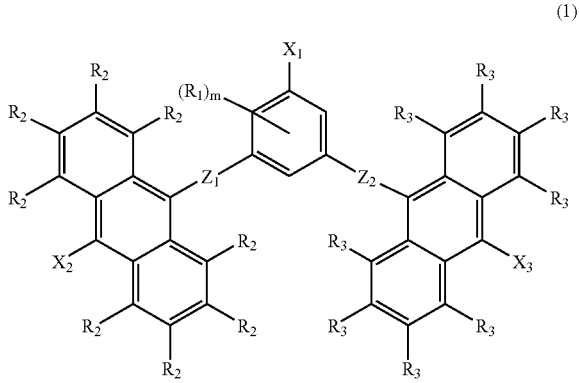

(Wherein $X_1$ is one selected from the group consisting of a hydrogen atom, a heavy hydrogen atom, a halogen atom, a substituted or unsubstituted alkyl group, aralkyl group, amino group, alkoxy group, sulfide group, aryl group, and heterocyclic group, and $X_1$ may be the same or different;

each of $X_2$ and $X_3$ is one selected from the group consisting of a heavy hydrogen atom, a substituted or unsubstituted alkyl group, alkenyl group, alkynyl group, aralkyl group, alkoxy group, and sulfide group, aryl groups including a substituted phenyl group, a substituted or unsubstituted terphenyl group, naphthyl group, phenanthryl group, pyrenyl group, tetracenyl group, and perylenyl group, a substituted or unsubstituted heterocyclic group, and a substituted silyl group, $X_2$ and $X_3$ may be the same or different, and, when $X_1$ is not an aryl group having an amino group, one of $X_2$ and $X_3$ may be a substituted or unsubstituted amino group, or a substituted or unsubstituted amino group having a coupling group;

each of $Z_1$ and $Z_2$ is one selected from the group consisting of a direct bond, a substituted or unsubstituted alkylene group, alkenylene group, alkynylene group, aralkylene group, arylene group, and divalent heterocyclic group, and a divalent substitutent having a coupling group, and $Z_1$ and $Z_2$ may be the same or different;

$R_1$ is one selected from the group consisting of a hydrogen atom, a heavy hydrogen atom, a halogen atom, a substituted or unsubstituted alkyl group, and alkoxy group, and $R_1$ may be the same or different;

each of $R_2$ and $R_3$ is one selected from the group consisting of a hydrogen atom, a heavy hydrogen atom, a halogen atom, a substituted or unsubstituted alkyl group, aryl group, alkoxy group, and amino group, and $R_2$ and $R_3$ may be the same or different; and m is an integer of 0 to 3.).

Furthermore, the present invention provides the substituted anthryl derivative described above, in which $X_1$ is represented by the following general formula (2):

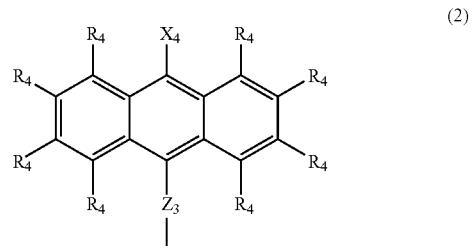

(Wherein $X_4$ is one selected from the group consisting of a hydrogen atom, a heavy hydrogen atom, a halogen atom, a substituted or unsubstituted alkyl group, alkenyl group, alkynyl group, aralkyl group, alkoxy group, and sulfide group, an amino group, an aryl group, a heterocyclic group, and a substituted silyl group, and $X_4$ may be the same or different;

$Z_3$ is one selected from the group consisting of a direct bond, a substituted or unsubstituted alkylene group, alkenylene group, alkynylene group, aralkylene group, arylene group, and divalent heterocyclic group, and a divalent substituent having a coupling group; and $R_4$ is one selected from the group consisting of a hydrogen atom, a heavy hydrogen atom, a halogen atom, a substituted or unsubstituted alkyl group, aryl group, alkoxy group, and amino group, and $R_4$ may be the same or different.).

Furthermore, the present invention provides the substituted anthryl derivative described above, in which $X_1$ is represented by the following general formula (3):

(3)

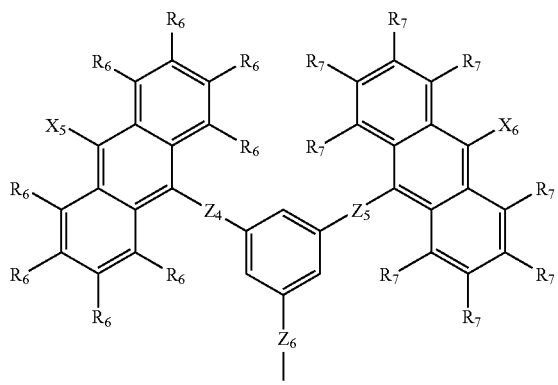

(Wherein each of $X_5$ and $X_6$ is one selected from the group consisting of a heavy hydrogen atom, a halogen atom, a substituted or unsubstituted alkyl group, alkenyl group, alkynyl group, aralkyl group, alkoxy group, and sulfide group, aryl groups including a substituted phenyl group, substituted or unsubstituted biphenyl group, terphenyl group, naphthyl group, phenanthryl group, pyrenyl group, tetracenyl group, and perylenyl group, a substituted or unsubstituted heterocyclic group, and a substituted silyl group, and $X_5$ and $X_6$ may be the same or different;

each of $Z_4$ and $Z_5$ is one selected from the group consisting of a direct bond, a substituted or unsubstituted alkylene group, alkenylene group, alkynylene group, aralkylene group, arylene group, and divalent heterocyclic group, and a divalent substituent having a coupling group, and $Z_4$ and $Z_5$ may be the same or different;

$Z_6$ is one selected from the group consisting of a direct bond, a substituted or unsubstituted alkylene group, alkenylene group, alkynylene group, and aralkylene group, arylene groups including a substituted or unsubstituted phenylene group, biphenylene group, terphenylene group, naphthylene group, fluorenylene group, phenanthrylene group, pyrenylene group, tetracenylene group, pentacenylene group, and perylenylene group, a substituted or unsubstituted divalent heterocyclic group, and a divalent substituent having a coupling group, and $Z_6$ may be the same or different;

each of $R_6$ and $R_7$ is one selected from the group consisting of a hydrogen atom, a heavy hydrogen atom, a halogen atom, a substituted or unsubstituted alkyl group, aryl group, alkoxy group, and amino group, and $R_6$ and $R_7$ may be the same or different; and n is an integer of 0 to 3.).

Furthermore, the present invention provides the substituted anthryl derivative described above, in which $X_1$ is an alkyl group.

Furthermore, the present invention provides the substituted anthryl derivative described above, in which at least one of $X_1$ to $X_3$, $Z_1$, $Z_2$, and $R_1$ to $R_3$ is a group containing a heavy hydrogen atom or a heavy hydrogen atom.

Furthermore, the present invention provides the substituted anthryl derivative described above, in which at least one of $X_2$ to $X_4$, $Z_1$ to $Z_3$, and $R_1$ to $R_4$ is a group containing a heavy hydrogen atom or a heavy hydrogen atom.

Furthermore, the present invention provides the substituted anthryl derivative described above, in which at least one of $X_2$, $X_3$, $X_5$, $X_6$, $Z_1$, $Z_2$, $Z_4$ to $Z_6$, $R_1$ to $R_3$, and $R_5$ to $R_7$ is a group containing a heavy hydrogen atom or a heavy hydrogen atom.

Furthermore, the present invention provides the substituted anthryl derivative described above, in which at least one of $X_1$ to $X_3$, $Z_1$, $Z_2$, and $R_1$ to $R_3$ is a group containing a heavy hydrogen atom or a heavy hydrogen atom.

Furthermore, the present invention provides an organic electroluminescence device including a pair of electrodes composed of an anode and a cathode at least one of which is transparent or translucent, and one or more organic compound layers sandwiched between the pair of electrodes, in which at least one of the organic compound layers contains at least one kind of the substituted anthryl derivatives described above.

Furthermore, the present invention provides an organic electroluminescence device including a light-emitting layer, a pair of electrodes composed of an anode and a cathode at least one of which is transparent or translucent, and one or more organic compound layers sandwiched between the pair of electrodes, in which the light-emitting layer contains at least one kind of the substituted anthryl derivatives described above.

The compounds each represented by the general formula (1) and the compounds each represented by the general formula (1) in which $X_1$ is represented by the general formula (2) or (3) can be predominantly used as materials for an organic EL device, respectively. Each of the compounds may be solely used in a light-emitting layer for a light-emitting purpose or may be used for a dopant or host material to produce a device having high color purity, high luminous efficiency, and long life.

One of the features of the compound represented by the general formula (1) or with $X_1$ represented by the general formula (2) or (3) is to contain at least two anthryl groups as a luminescent unit with high luminous efficiency in a benzene ring core with each of the anthryl groups having a substituent such as an amino group, an amino group with a coupling group, or an aryl group. Luminescence colors of blue, green, and other colors at longer wavelengths can be obtained by adjusting the HOMO/LUMO level of the material by the change of the substituent on the anthryl group. When the above compound is used as a dopant material, the desired material can be easily designed and synthesized on the basis of the HOMO/LUMO level of the host material by making a prediction as to the HOMO/LUMO level of the material by calculation with respect to the change of the substituent on the anthryl group (e.g., the HOMO/LUMO level of the exemplified compound 19 calculated with B3LYP/3-21G is −4.846/−1.767). In addition, the same is applied when the above compound is used as a host material. Furthermore, the above compounds permit easy molecular design in consideration of their energy levels against the hole-transporting layer and the electron-transporting layer. The cohesion between molecules can be prevented by introducing a steric hindrance group or a fluorine atom having a large electronegativity which tends to cause an electrostatic repulsion to a proximal molecule into the substituent on the benzene ring core, the anthryl group, the aryl group, the amino group, or the like, and such introduction can be particularly expected to extend the life of the device. As to the thermal characteristics of the device, a material having good film-forming ability and thermal stability can be obtained when the compound adopts the form of a star-burst type dendritic molecule. In addition to the above consideration, the material of the present invention has considered the introduction of a molecule unit substituted with heavy hydrogen by an isotope effect in consideration of inhibition of molecular vibration and thermal inactivation. The present invention has been achieved by performing molecular design on the basis of the above consideration.

Furthermore, when the compound is used as a dopant material, the concentration of the dopant against the host material is 0.01% to 80%, preferably 1% to 40%. The dopant material may be distributed in a layer made of the host material uniformly or with a concentration gradient, or may be partially distributed in a certain region of the host material layer to allow the layer to have a region containing no dopant material.

Hereinafter, the present invention will be described in detail.

Given below are specific examples of the substituents in the compounds represented by the general formula (1) and the compounds represented by the general formula (1) in which $X_1$ is represented by the general formula (2) or (3).

Specific examples of the coupling group and the substituent in the general formulae (1) to (3) described above are as follows:

Examples of a coupling group in each of the above general formulae (1) to (3) include, but not limited to, a substituted or unsubstituted arylene group and divalent heterocyclic group.

Examples of a divalent substituent having a coupling group in each of the above general formulae (1) to (3) include, but not limited to, a substituted or unsubstituted alkylene group, alkenylene group, alkynylene group, aralkylene group, and amino group, and a substituted silyl group, ether group, thioether group, and carbonyl group.

Examples of a substituted or unsubstituted alkyl group include, but not limited to, a methyl group, a methyl-d1 group, a methyl-d3 group, an ethyl group, an ethyl-d5 group, an n-propyl group, an n-butyl group, an n-pentyl group, an n-hexyl group, an n-heptyl group, an n-octyl group, an n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group.

Examples of a substituted or unsubstituted aralkyl group include, but not limited to, a benzyl group, a 2-phenylethyl group, a 2-phenylisopropyl group, a 1-naphthylmethyl group, a 2-naphthylmethyl group, a 2-(1-napthyl)ethyl group, a 2-(2-napthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, and a 4-bromobenzyl group.

Examples of a substituted or unsubstituted alkenyl group include, but not limited to, a vinyl group, an allyl group (2-propenyl group), a 1-propenyl group, an iso-propenyl group, a 1-butenyl group, a 2-butenyl group, a 3-butenyl group, and a styryl group.

Examples of a substituted or unsubstituted alkynyl group include, but not limited to, an acetylenyl group, a phenylacetylenyl group, and a 1-propynyl group.

Examples of a substituted or unsubstituted aryl group include, but not limited to, a phenyl group, a phenyl-d5 group, a 4-methylphenyl group, a 4-methoxyphenyl group, a 4-ethylphenyl group, a 4-fluorophenyl group, a 4-trifluorophenyl group, a 3,5-dimethylphenyl group, a 2,6-diethylphenyl group, a mesityl group, a 4-tert-butylphenyl group, a ditolylaminophenyl group, a biphenyl group, a terphenyl group, a 1-naphthyl group, a 2-naphthyl group, a 1-naphthyl-d7 group, a 2-naphthyl-d7 group, a 1-anthryl group, a 2-anthryl group, a 9-anthryl group, a 9-anthryl-d9 group, a 2-phenanthryl group, a 3-phenanthryl group, a 4-phenanthryl group, a 9-phenanthryl group, a 9-phenanthryl-d9 group, a 1-pyrenyl group, a 1-pyrenyl-d9 group, a 2-pyrenyl group, a 4-pyrenyl group, a tetracenyl group, a pentacenyl group, a fluorenyl group, a triphenylenyl group, and a perylenyl group.

Examples of a substituted or unsubstituted heterocyclic group include, but not limited to, a pyrrolyl group, a pyridyl group, a pyridyl-d5 group, a bipyridyl group, a methylpyridyl group, a terpyrrolyl group, a thienyl group, a thienyl-d4 group, a terthienyl group, a propylthienyl group, a furyl group, a furyl-d4 group, an indolyl group, a 1,10-phenanthroline group, a phenazinyl group, a quinolyl group, a carbazolyl group, an oxazolyl group, an oxadiazolyl group, a thiazolyl group, and a thiadiazolyl group.

Examples of a substituted or unsubstituted alkylene group include, but not limited to, a methylene group, a methylene-d2 group, a difluoromethylene group, an ethylene group, an ethylene-d4 group, a perfluoroethylene group, a propylene group, an iso-propylene group, a butylene group, and a 2,2-dimethylpropylene group.

Examples of a substituted or unsubstituted aralkylene group include, but not limited to, a benzylene group, a 2-phenylethylene group, a 2-phenylisopropylene group, a 1-naphthylmethylene group, a 2-naphthylmethylene group, a 9-anthrylmethylene group, a 2-fluorobenzylene group, a 3-fluorobenzylene group, a 4-fluorobenzylene group, a 4-chlorobenzyl group, and a 4-bromobenyzlene group.

Examples of a substituted or unsubstituted alkenyl group include, but not limited to, a vinylene group, an iso-propenylene group, a styrylene group, and a 1,2-diphenylvinylene group.

Examples of a substituted or unsubstituted alkynyl group include, but not limited to, an acetylenylene group and a phenyl acetylenylene group.

Examples of a substituted or unsubstituted arylene group include, but not limited to, a phenylene group, a biphenylene group, a tetrafluorophenylene group, a dimethylphenylene group, a naphthylene group, an anthrylene group, a phenanthrylene group, a pyrenylene group, a tetracenylene group, a pentacenylene group, and a perylenylene group.

Examples of a substituted or unsubstituted divalent heterocyclic group include, but not limited to, a furylene group, a pyrrorylene group, a pyridilene group, a terpyridilene group, a thienylene group, a terthienylene group, an oxazolylene group, a thiazolylene group, and a carbazolylene group.

In a substituted or unsubstituted amino (—NR'R") group, each of R' and R" is a hydrogen atom, a heavy hydrogen atom, the above substituted or unsubstituted alkyl group, aralkyl group, aryl group, or heterocyclic group, an alkylene group, alkenylene group, alkynylene group, aralkylene group, and amino group having a coupling group derived from a substituted or unsubstituted arylene group, or divalent heterocyclic group, a substituted silyl group, ether group, thioether group, and carbonyl group. Examples of the substituted or unsubstituted amino group include, but not limited to, an amino group, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N-phenyl-N-tolylamino group, an N,N-ditolylamino group, an N-methyl-N-phenylamino group, an N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Examples of a substituted or unsubstituted alkoxy group include: an alkyloxy group and aralkyloxy group having the above substituted or unsubstituted alkyl group, or aralkyl group; and an aryloxy group having the above substituted or unsubstituted aryl group or heterocyclic group. Specific examples thereof include, but not limited to, a methoxy group, an ethoxy group, a propoxy group, a 2-ethyl-octyloxy group, a phenoxy group, a 4-tert-butylphenoxy group, a benzyloxy group, and a thienyloxy group.

Examples of a substituted or unsubstituted sulfide group include: an alkylsulfide group or aralkylsulfide group having the above substituted or unsubstituted alkyl group, or aralkyl group; and an arylsulfide group having the above substituted or unsubstituted aryl group or heterocyclic group. Specific examples thereof include, but not limited to, a methylsulfide group, an ethylsulfide group, a phenylsulfide group, and a 4-methylphenylsulfide group.

Examples of substituents which the above substituents and coupling groups may additionally have include, but not limited to: a heavy hydrogen atom; alkyl groups such as a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a benzyl group, and a 2-phenylethyl group; alkoxy groups such as an aralkyl group, a methoxy group, an ethoxy group, a propoxy group, a 2-ethyl-octyloxy group, a phenoxy group, a 4-tert-butylphenoxy group, and a benzyloxy group; aryl groups such as a phenyl group, a 4-methylphenyl group, a 4-ethylphenyl group, a 3-chlorophenyl group, a 3,5-dimethylphenyl group, a triphenylamino group, a biphenyl group, a terphenyl group, a naphthyl group, an anthryl group, a phenanthryl group, and a pyrenyl group; heterocyclic groups such as a pyridyl group, a bipyridyl group, a methylpyridyl group, a thienyl group, a terthienyl group, a propylthienyl group, a furyl group, a quinolyl group, a carbazolyl group, and an N-ethylcarbazolyl group; halogen groups; a hydroxyl group; a cyano group; and a nitro group.

Next, typical compounds represented by the general formula (1) and by the general formula (1) in which $X_1$ is represented by the general formula (2) or (3) will be given. However, the present invention is not limited to those compounds.

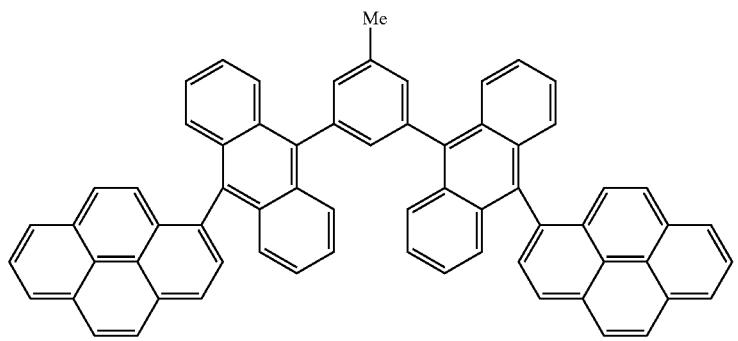

1

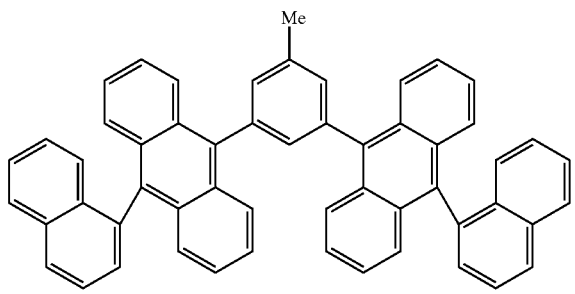

2

3
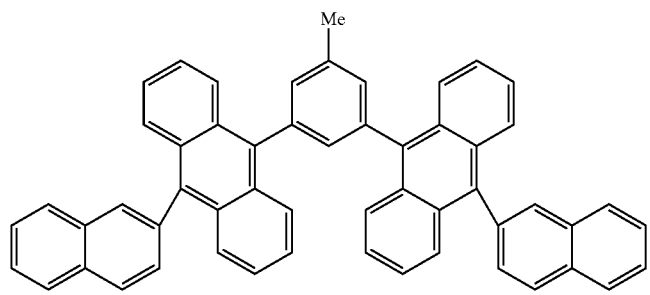
4
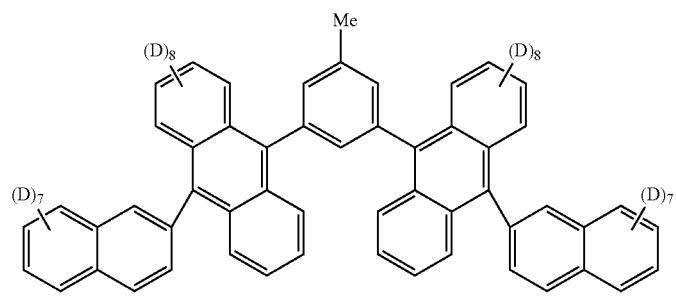
5
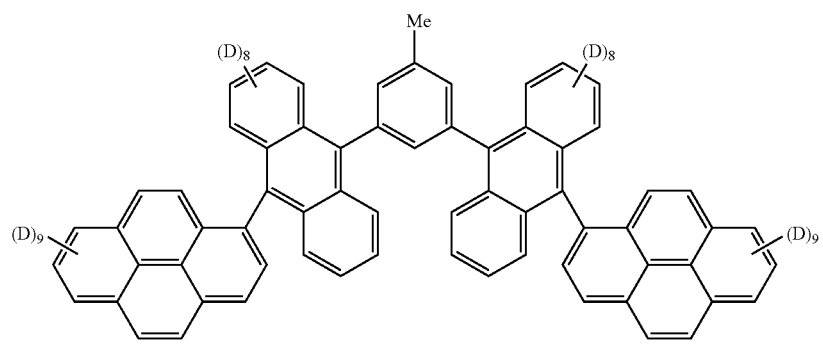
6
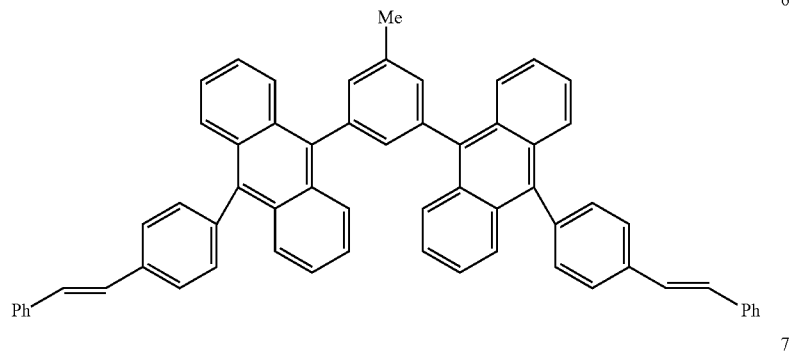
7
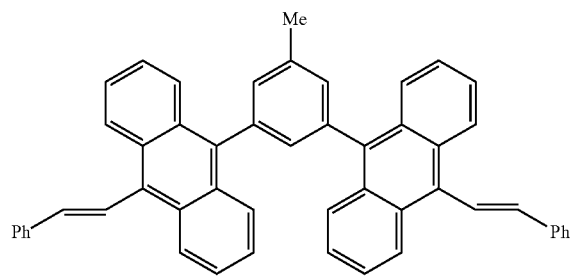

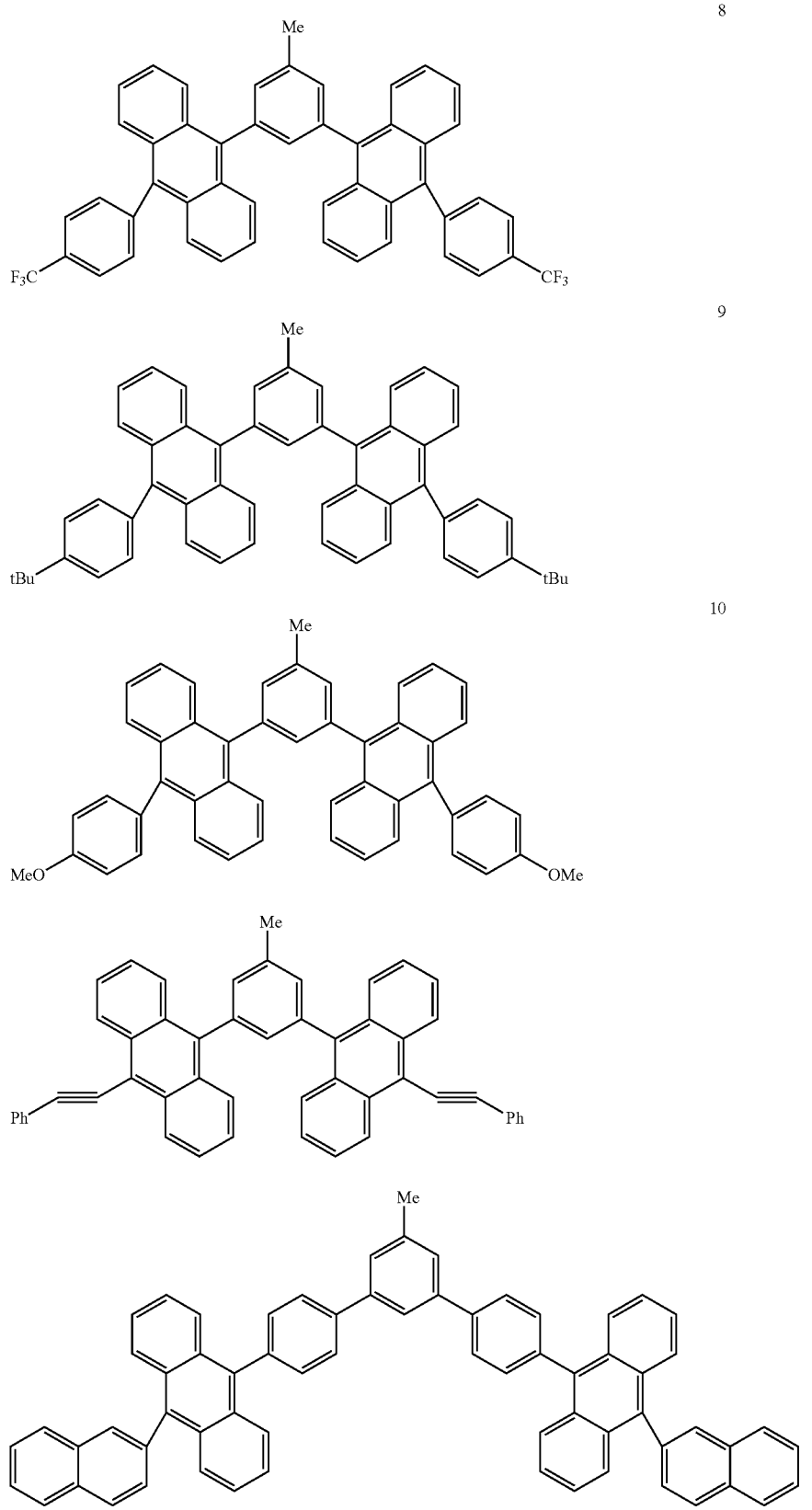

-continued
13
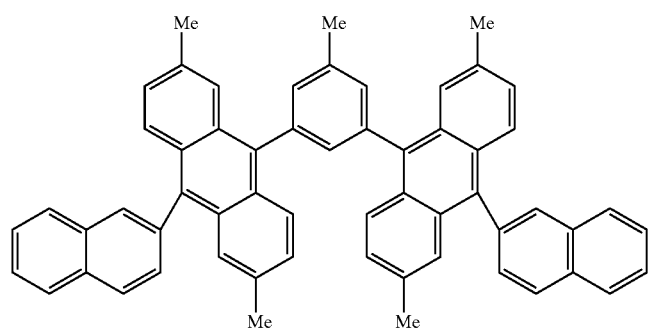
14
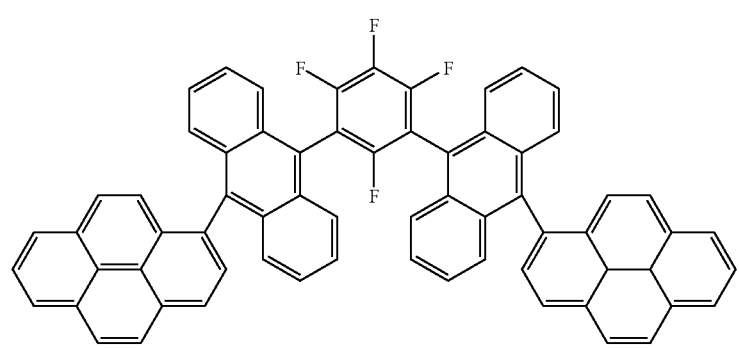
15
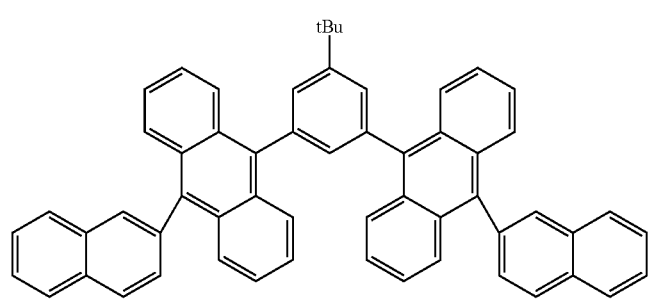
16
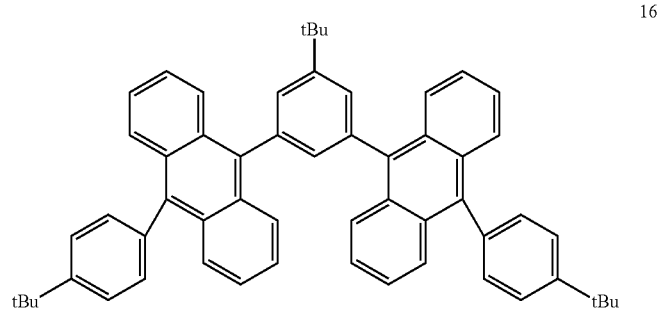
17
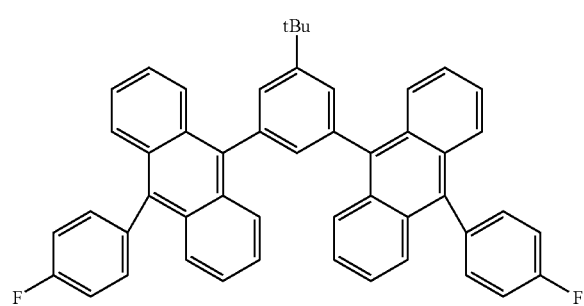

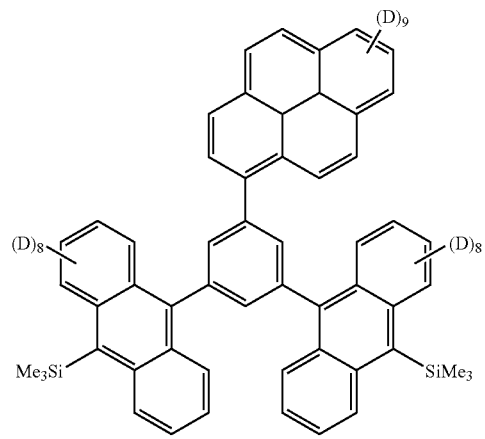
18
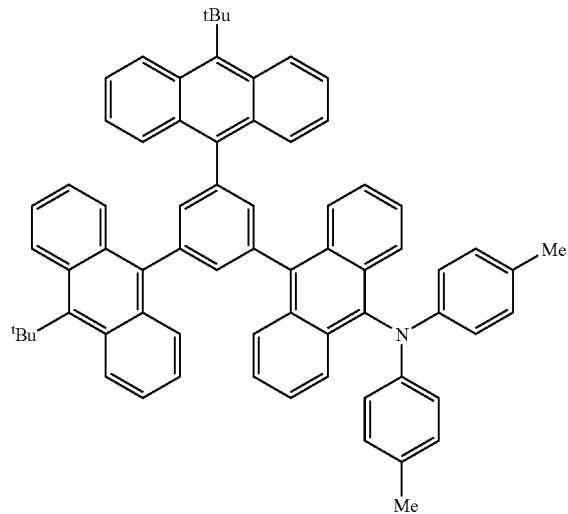
19
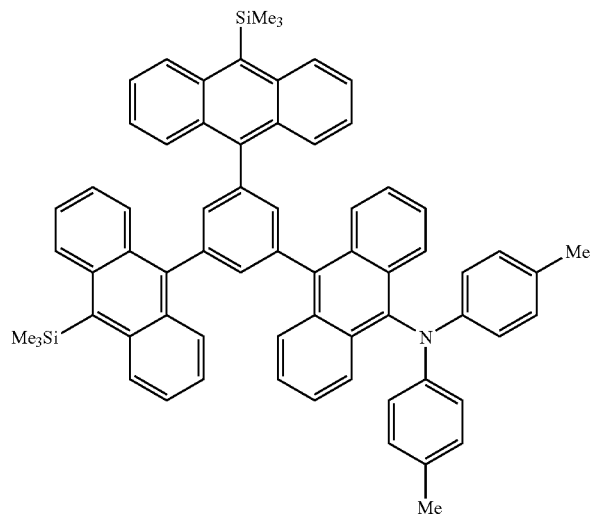
20

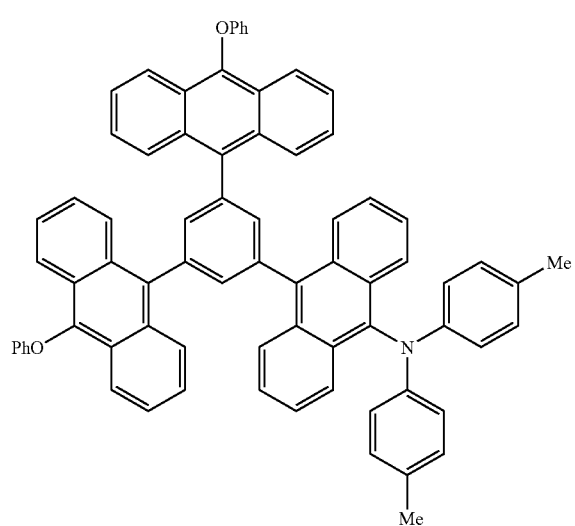
21
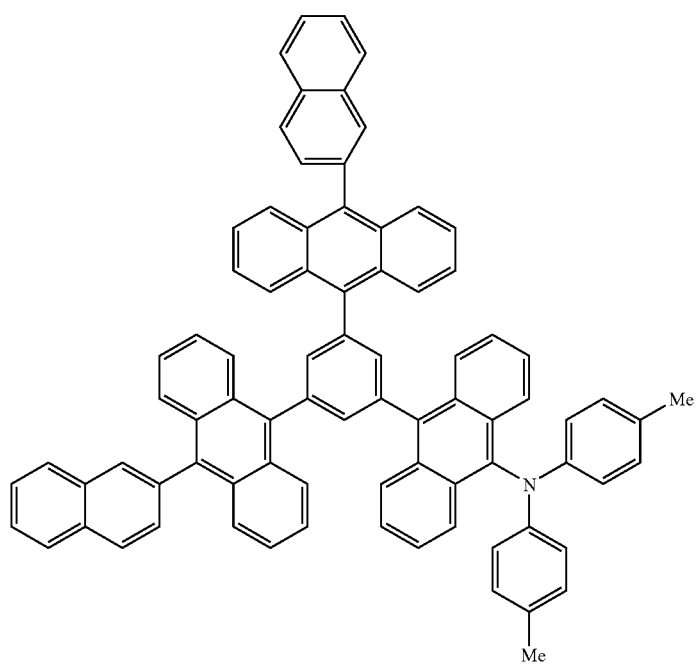
22

-continued
23
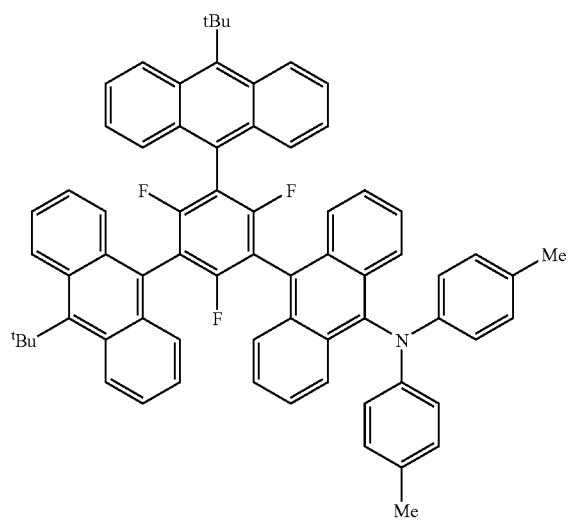
24
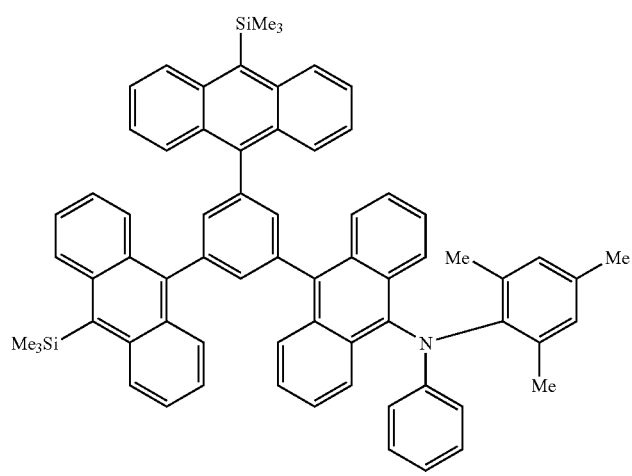
25
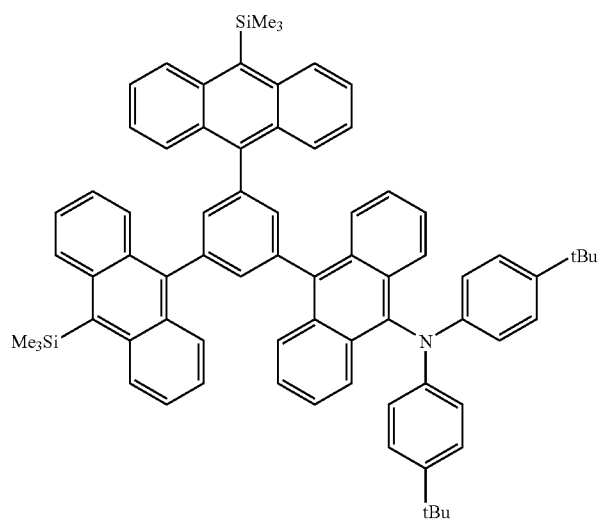

-continued
26
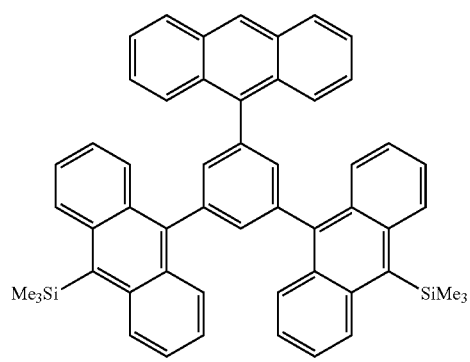
27
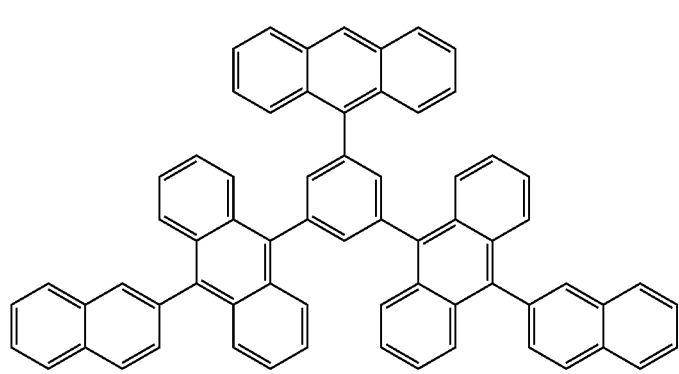
28
29
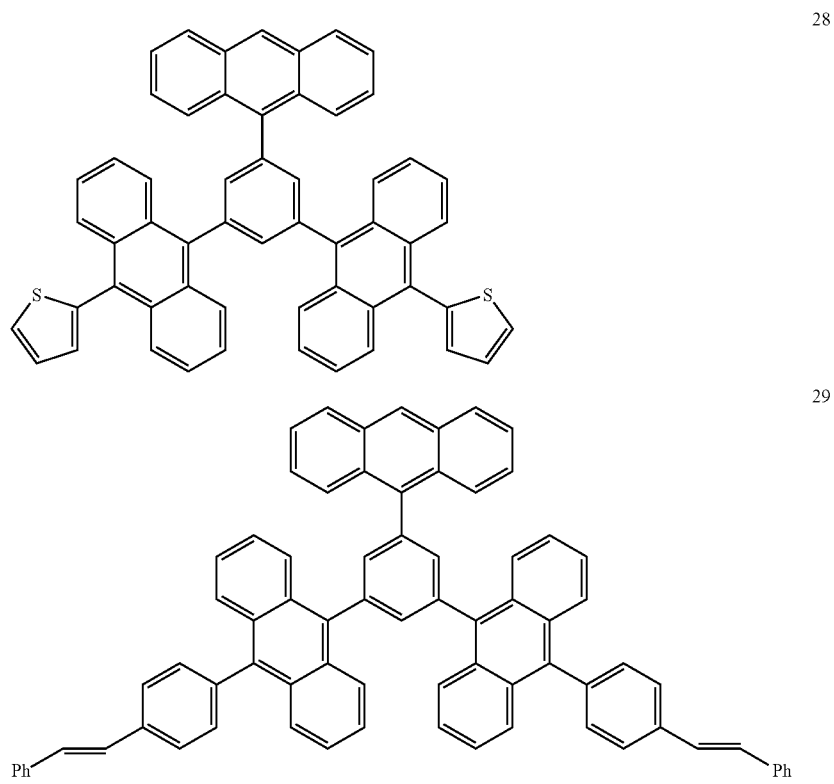

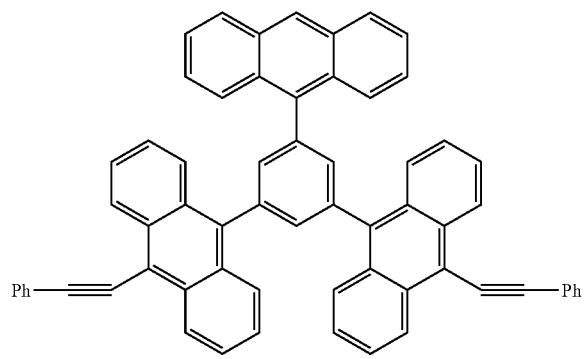
30
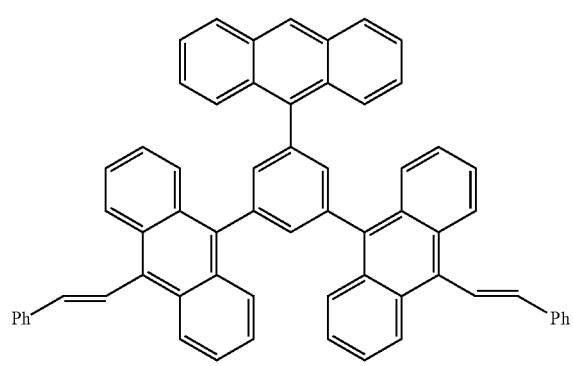
31
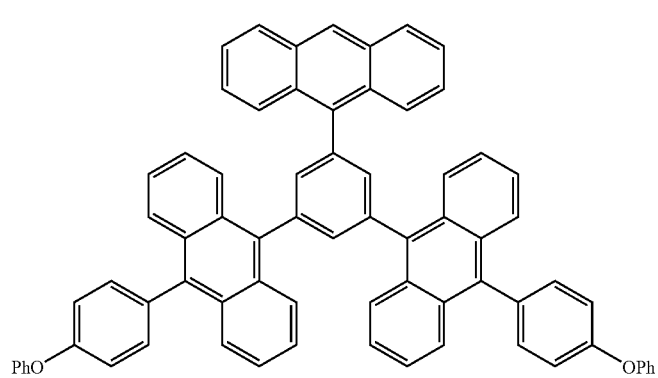
32
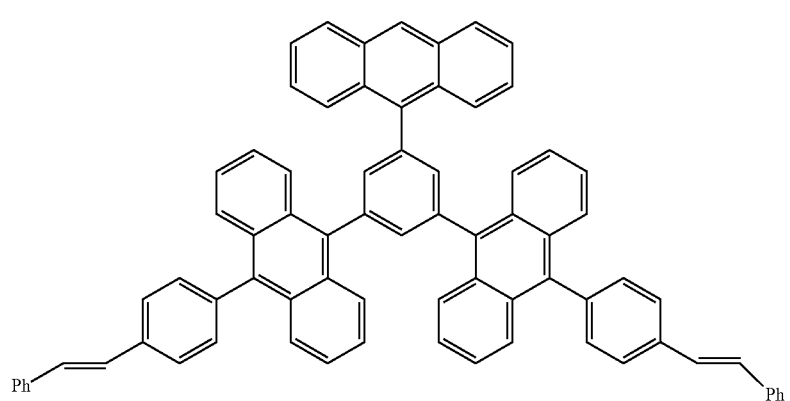
33

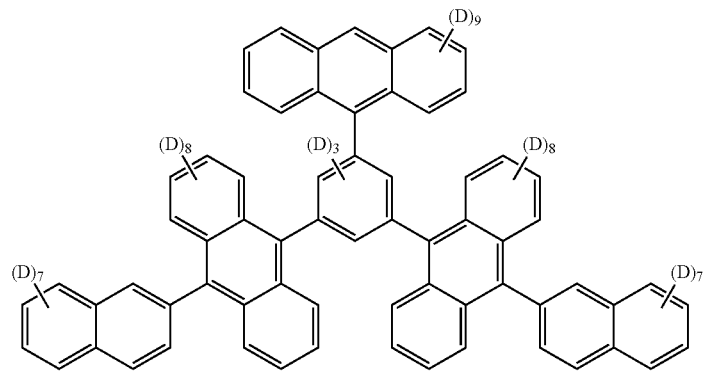
34
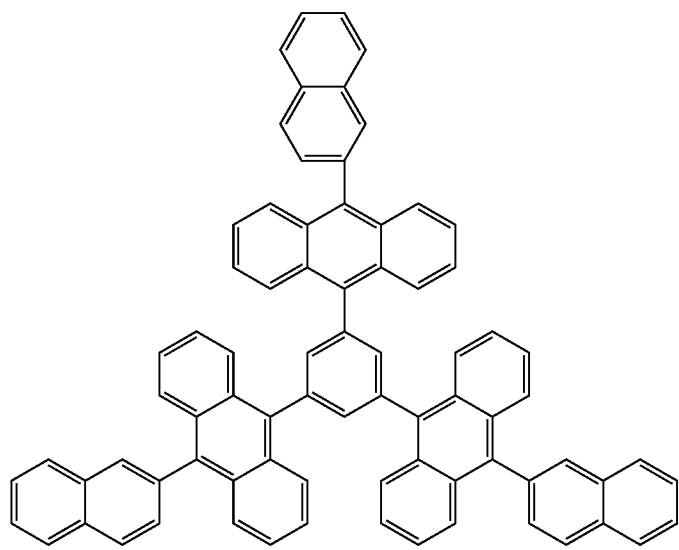
35
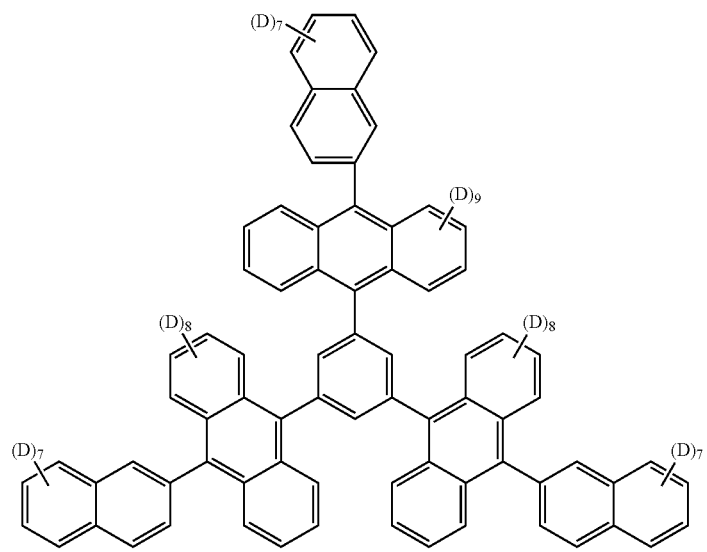
36

-continued
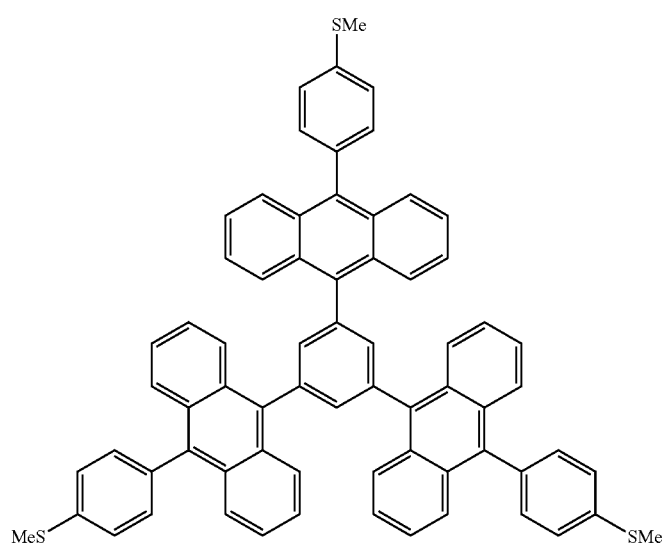
37
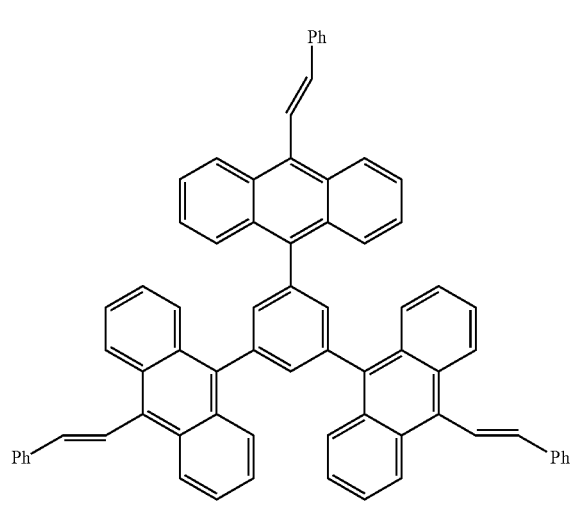
38
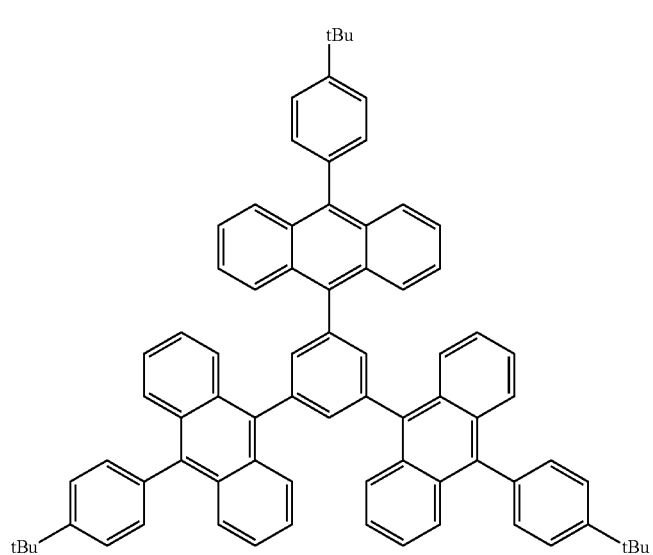
39

-continued
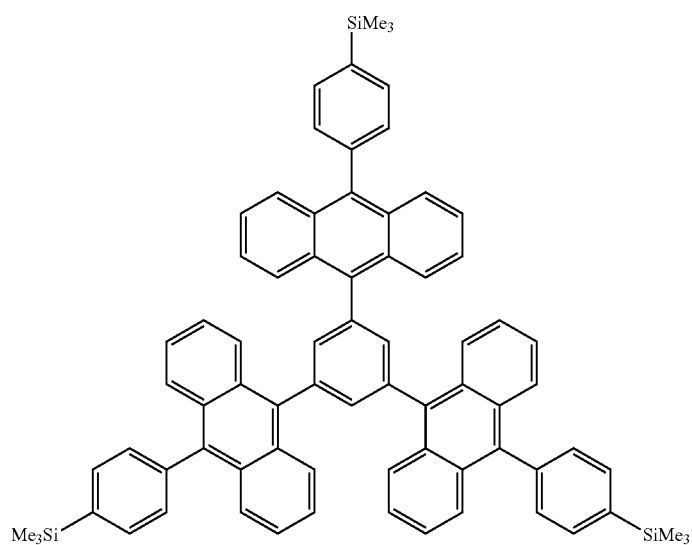
40
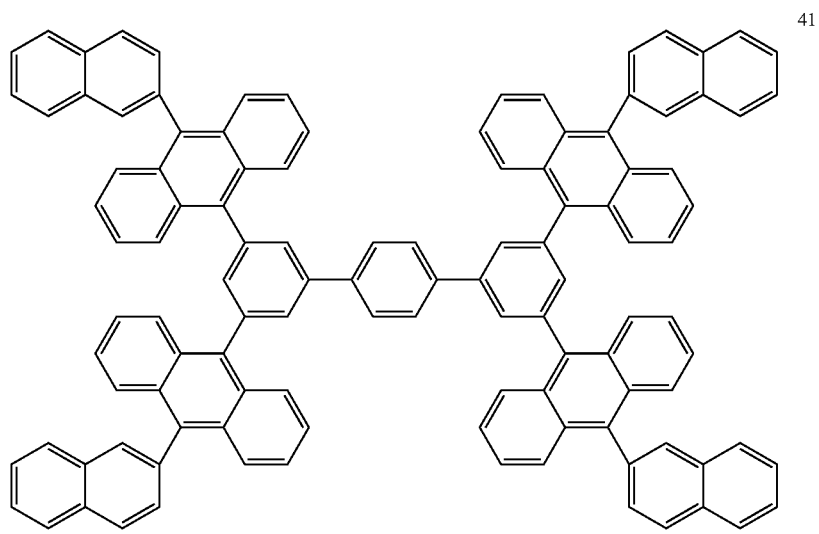
41
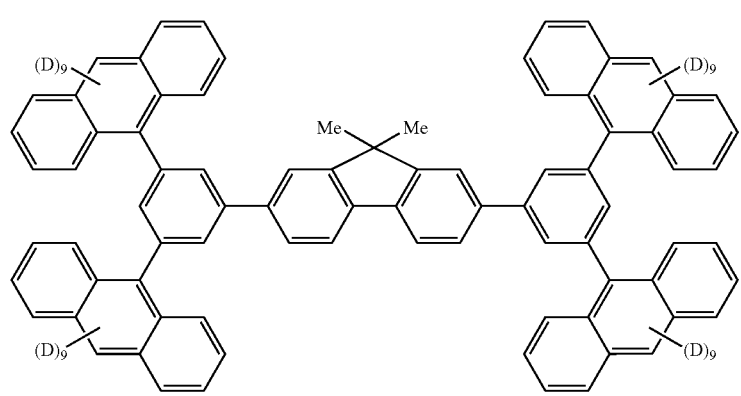
42

-continued

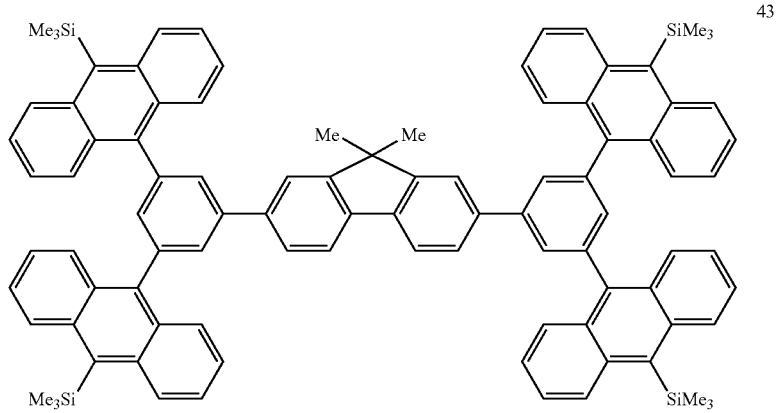

43

Next, the organic EL device of the present invention will be described in detail.

The organic EL device of the present invention includes a pair of electrodes consisting of an anode and a cathode and one or more organic-compound-containing layers. At least one of the organic-compound-containing layers contains at least one of the compounds represented by the general formula (1) or the general formula (1) in which $X_1$ is a compound represented by the general formula (2) or (3).

FIGS. 1 to 5 show preferable embodiments of the organic EL device of the present invention.

FIG. 1 is a cross sectional diagram that illustrates an organic EL device as one of the embodiments of the present invention. As shown in the figure, the device is constructed by mounting an anode 2, a light-emitting layer 3, and a cathode 4 on a substrate 1 in that order. The electroluminescence device used herein is useful in the case where the device has a hole-transporting ability, an electron-transporting ability, and a light-emitting ability by itself or where compounds having the respective properties are used in combination.

Figure 2:
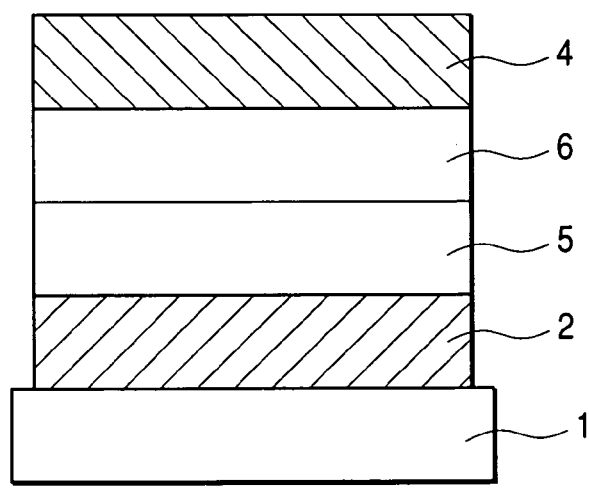
FIG. 2 is a cross sectional diagram illustrating another embodiment of the organic EL device of the present invention.

FIG. 2 is a cross sectional diagram that illustrates an organic EL device as another embodiment of the present invention. As shown in the figure, the device is constructed by mounting an anode 2, a hole-transporting layer 5, an electron-transporting layer 6, and a cathode 4 on a substrate 1 in that order. In this case, a light-emitting material is useful when it is used in combination with merely a non-illuminant hole-transporting or electron-transporting material using materials having hole-transporting ability or electron-transporting ability or both of them in the respective layers. In this case, furthermore, the light-emitting layer 3 is constructed of the hole-transporting layer 5 or the electron-transporting layer 6.

Figure 3:
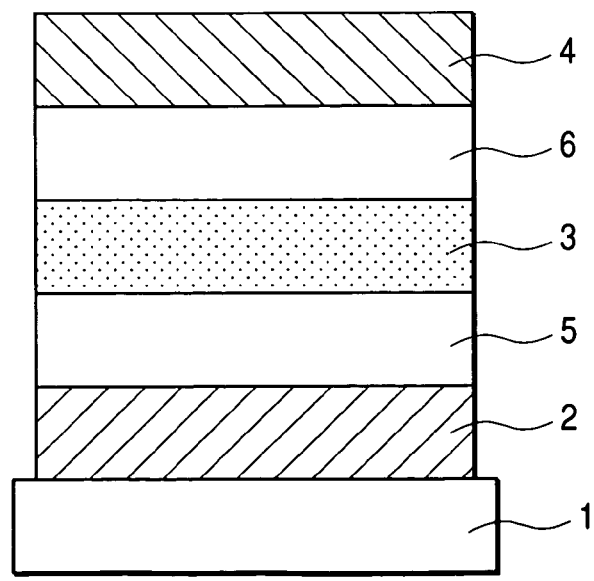
FIG. 3 is a cross sectional diagram illustrating another embodiment of the organic EL device of the present invention.

FIG. 3 is a cross sectional diagram that illustrates an organic EL device as another embodiment of the present invention. As shown in the figure, the device is constructed by mounting an anode 2, a hole-transporting layer 5, a light-emitting layer 3, an electron-transporting layer 6, and a cathode 4 on a substrate 1 in that order. In this case, the carrier-transporting function and the light-emitting function are separated from each other. The device is used in combination with compounds having hole-transporting ability, electron-transporting ability, and light-emitting ability as appropriate, allowing a substantial increase in flexibility for material choice. Simultaneously, various kinds of compounds having different emission wavelengths can be used, allowing an increase in variety of luminescence hue. Furthermore, an increase in luminous efficiency may be ensured by effectively closing each carrier or exciton in the middle light-emitting layer 3.

Figure 4:
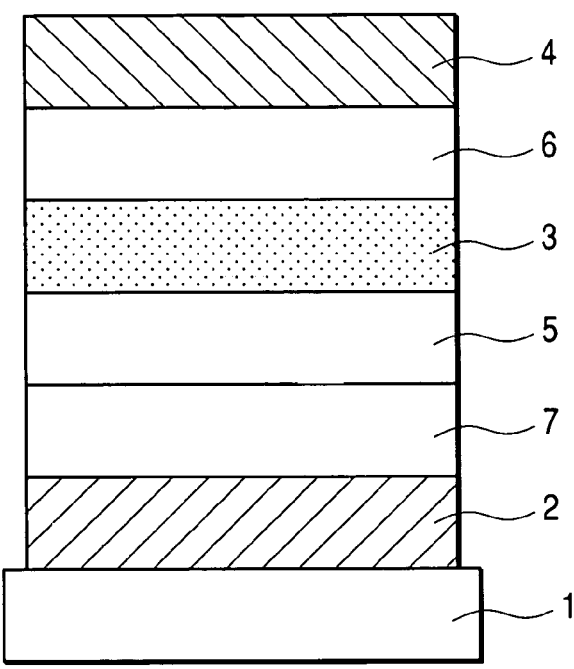
FIG. 4 is a cross sectional diagram illustrating another embodiment of the organic EL device of the present invention.

FIG. 4 is a cross sectional diagram that illustrates an organic EL device as another embodiment of the present invention. In this figure, comparing with the device shown in FIG. 3, the device is constructed such that a hole-injection layer 7 is inserted in the layer structure on the anode side (i.e., between the hole-transporting layer 5 and the anode 2). Therefore it is effective in improving the absolute contact between the anode 2 and the hole-transporting layer 5 or improving the hole-injecting ability, so that such a configuration of the device will be advantageous in lowering the voltage of the device.

Figure 5:
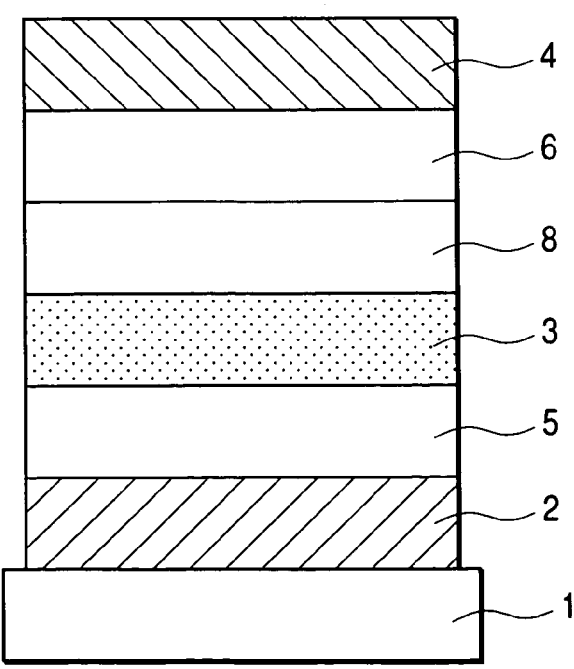
FIG. 5 is a cross sectional diagram illustrating another embodiment of the organic EL device of the present invention.

FIG. 5 is a cross sectional diagram that illustrates an organic EL device as another embodiment of the present invention. In this figure, comparing with the device shown in FIG. 3, a layer for blocking the travel of a hole or exciton to the cathode 4 (a hole/exciton-blocking layer 8) is inserted between the light-emitting layer 3 and the electron-transporting layer 6. Using a compound having an extremely high ionization potential as the hole/exciton-blocking layer 8 allows the configuration of the device to be effective in improving luminous efficiency.

However, all of the devices represented by FIGS. 1 to 5 are substantially fundamental device structures, so that the configuration of the organic EL device using the compound of the present invention is not limited to these examples. For instance, various kinds of layer structures may be configured, such as the formation of an insulating layer on the boundary surface between an electrode and an organic layer, the formation of an adhesive or interference layer, or the formation of a hole-transporting layer composed of two layers with different ionization potentials.

The compound used in the present invention, which is represented by the general formula (1) or by the general formula (1) in which $X_1$ is represented by the general formula (2) or (3), can be used in each of the configurations of FIGS. 1 to 5.

In particular, an organic layer using the compound of the present invention is useful as a light-emitting layer, an electron-transporting layer, or a hole-transporting layer. In addition, a layer formed by a vacuum deposition method, a solution coating method, or the like is hardly crystallized, so that the layer will be excellent in chronological stability.

In the present invention, the compound represented by the general formula (1) or by the general formula (1) in which $X_1$ is represented by the general formula (2) or (3) is used and may be used in combination with a conventionally known hole-transportable compound, light-emitable compound, electron-transportable compound, or the like as required.

Those compounds will be exemplified below.

A preferable hole-injection transportable material has excellent mobility to make the injection of a hole from an anode easy and to transport the injected hole to a light-emitting layer. Low molecular and high molecular materials having hole-injecting and transporting abilities include a triarylamine derivative, a phenylene diamine derivative, a triazole derivative, an oxadiazole derivative, an imidazole derivative, a pyrazoline derivative, a pyrazolone derivative, an oxazole derivative, a fluorenone derivative, a hydrazone derivative, a stilbene derivative, a phthalocyanine derivative, a porphyrin derivative, and poly (vinylcarbazole), poly (silylene), poly (thiophene), and other conductive polymers. However, the material is not limited to those compounds. Hereinafter, some of the specific examples of the material will be described.

Low molecular material having hole injecting and transporting abilities

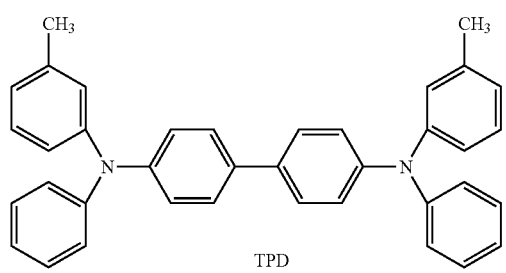

TPD

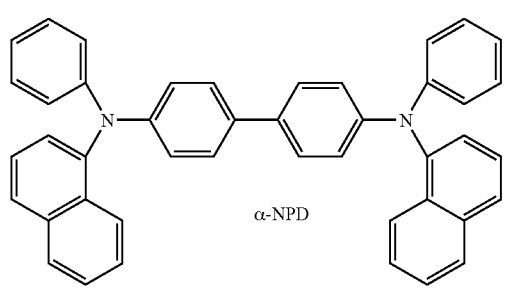

α-NPD

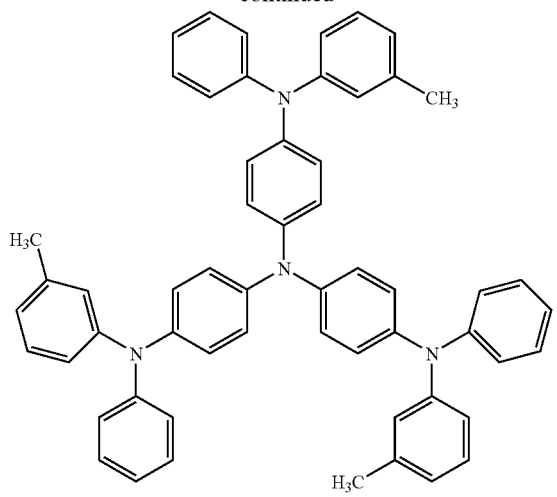

m-MTDATA

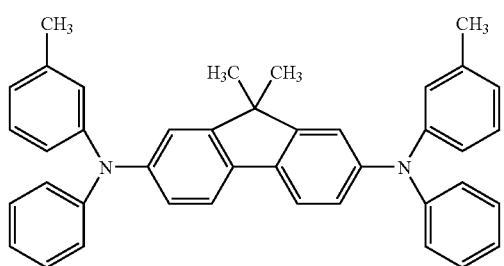

DTDPFL

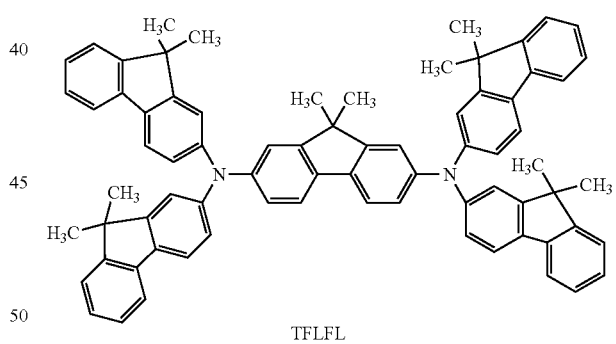

TFLFL

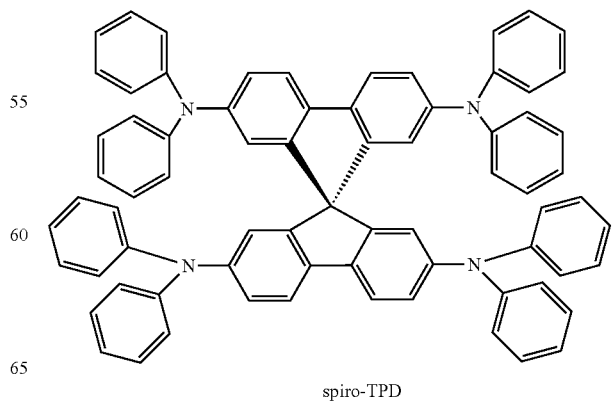

spiro-TPD

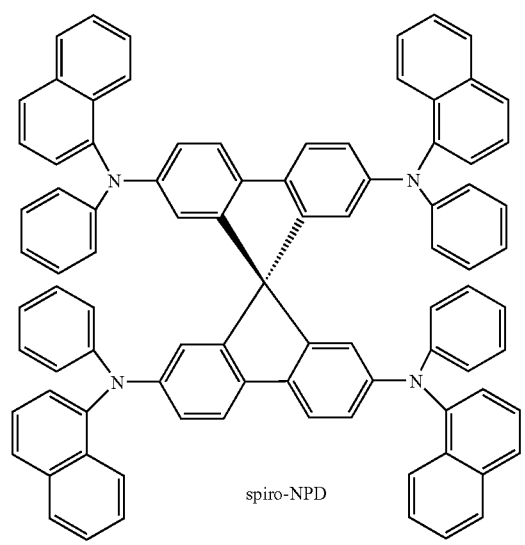
spiro-NPD
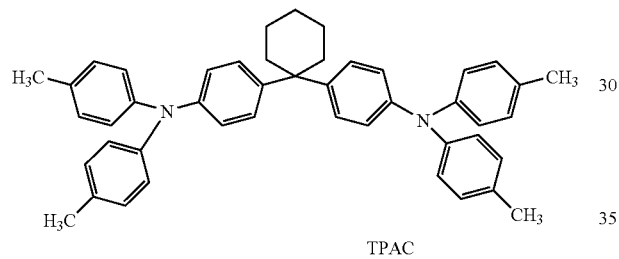
TPAC
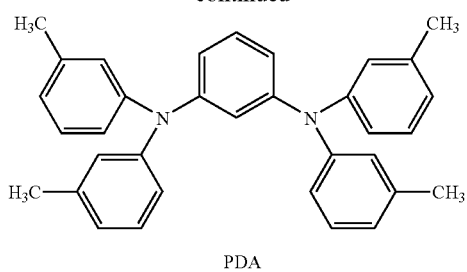
PDA
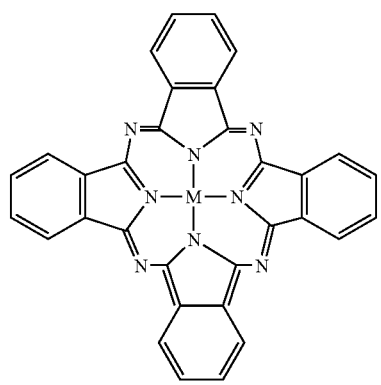
Pc-M
M: Cu, Mg, AlCl,
MnCl, GaCl, etc
High molecular material having hole injecting and transporting abilities
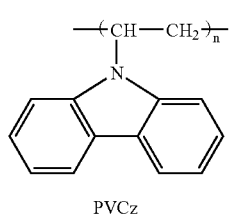
PVCz
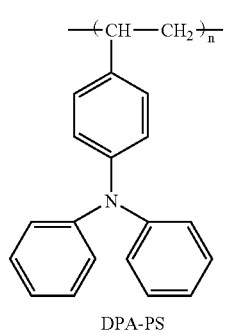
DPA-PS
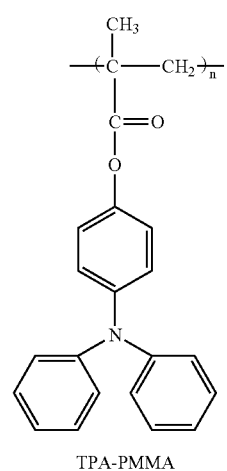
TPA-PMMA -continued
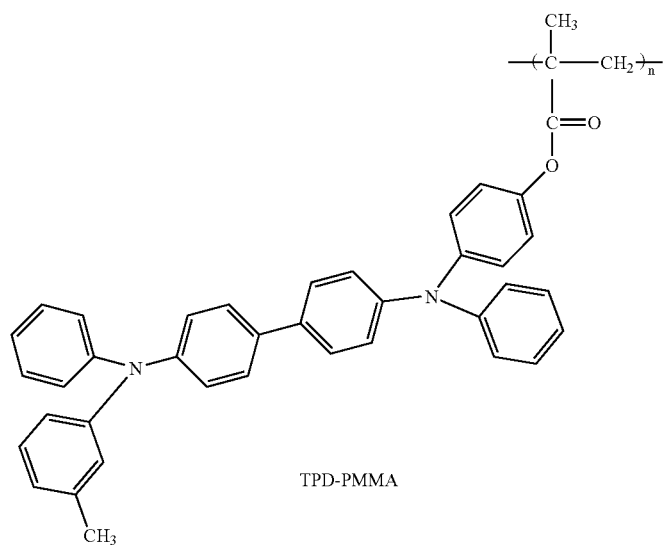
TPD-PMMA
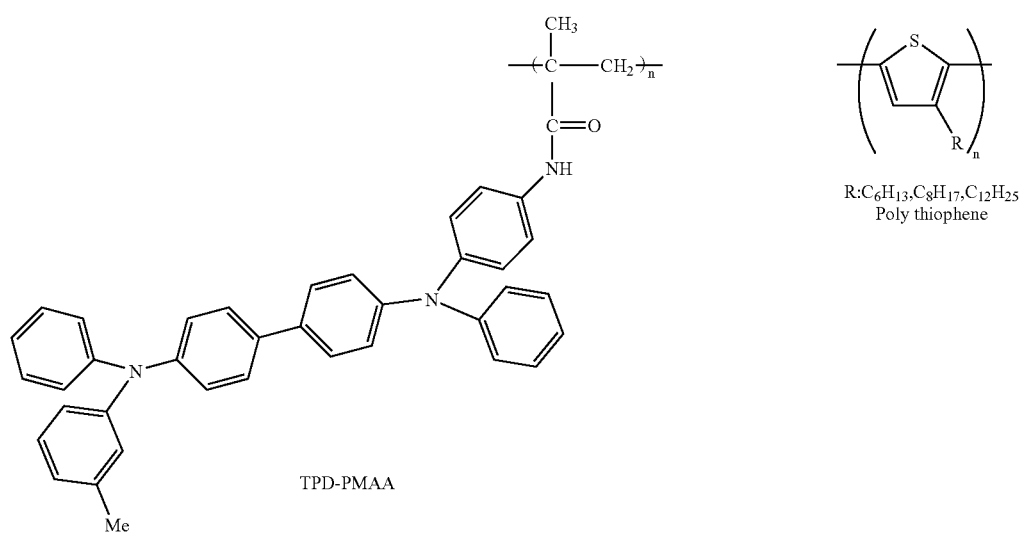
TPD-PMAA
R:$C_6H_{13}$,$C_8H_{17}$,$C_{12}H_{25}$
Poly thiophene
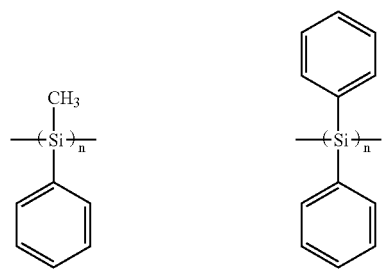
Polysilane -continued

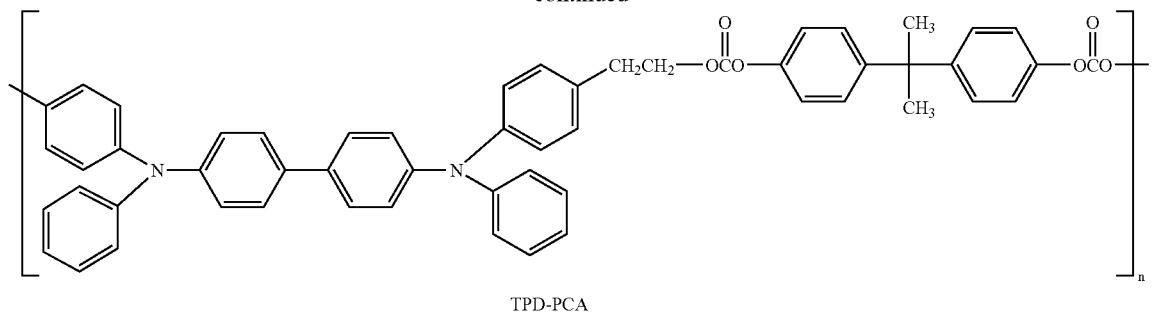

TPD-PCA

Examples of available materials which are mainly involved in a light-emitting function except the anthryl derivative group substitute compound represented by the general formulae (1) and (2) include, but not limited to: polycyclic condensed aromatic compounds (including naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, and rubrene); quinacridone derivatives; acridone derivatives; coumarin derivatives; pyran derivatives; Nile red; pyrazine derivatives; benzoimidazole derivatives; benzothiazole derivatives; benzoxazole derivatives; stilbene derivatives; organometallic complexes (including organic aluminum complexes such as tris(8-quinolinolato)aluminum and organic beryllium complexes); and high-molecular derivatives such as poly(phenylene vinylene) derivatives, poly(fluorene) derivatives, poly(phenylene) derivatives, poly(thienylene vinylene) derivatives, and poly(acetylene) derivatives. Part of the specific examples will be shown below.

Low Molecular Light-Emitting Material

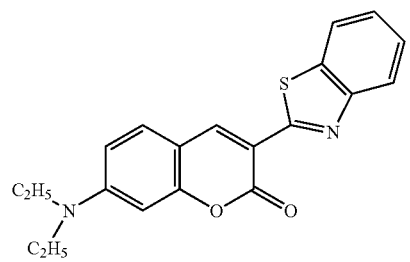

Coumarin 6

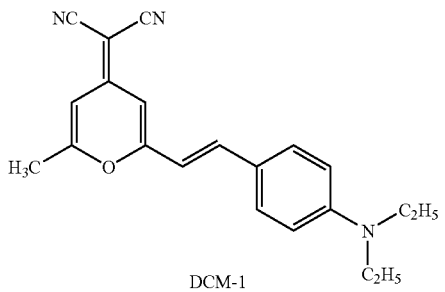

DCM-1

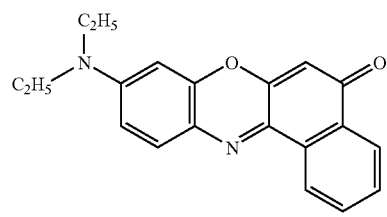

Nile red

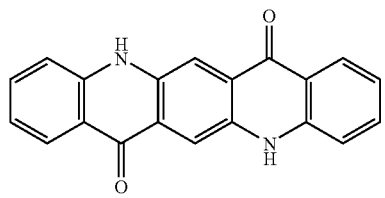

Quinacridone

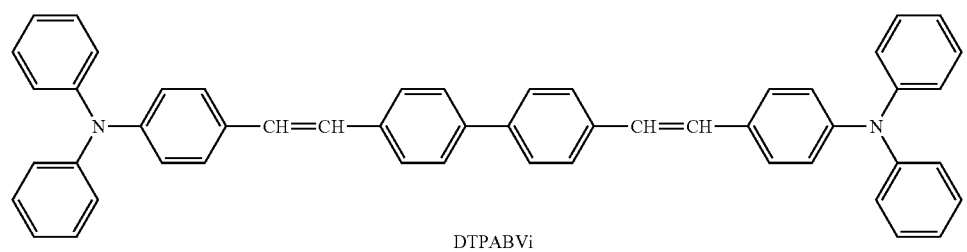

DTPABVi

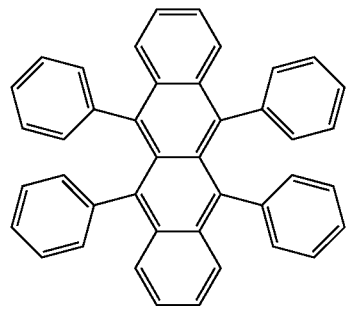
Rubrene
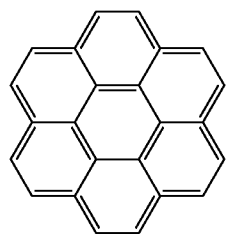
Coronene
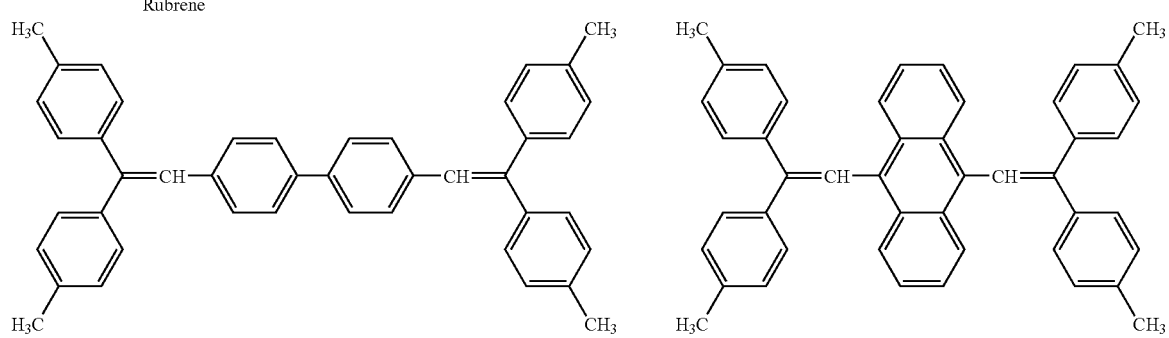
High Molecular Light-Emitting Material
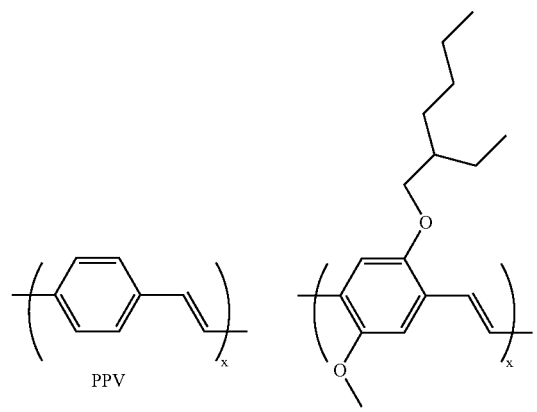
PPV
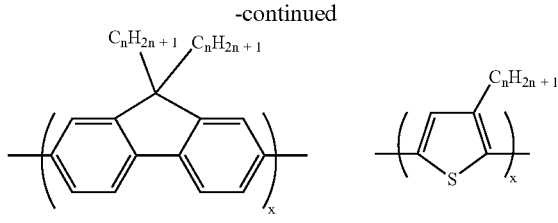
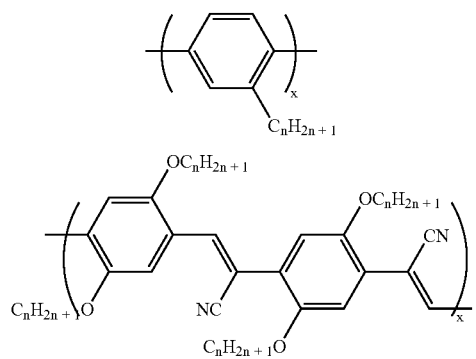
Metal Complex Light-Emitting Material
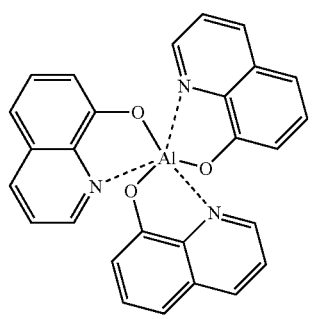
Alq -continued

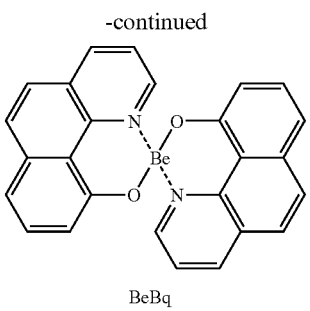
BeBq

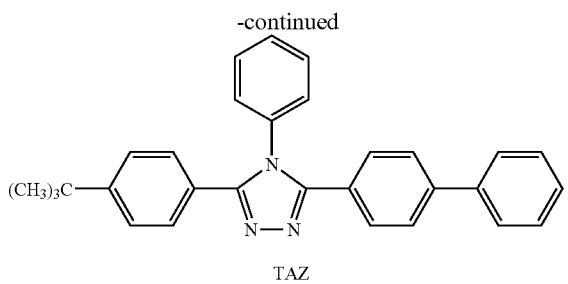
TAZ

The material having electron injecting and transporting abilities may be optionally chosen from materials that simplify the injection of an electron from a cathode, and that have a function of transporting the injected electron into the light-emitting layer. The material is chosen by considering the balance with the mobility of the carrier of the hole-transporting material. Examples of the material having electron injecting and transporting abilities include, but not limited to, oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organometallic complexes. Part of the specific examples will be shown below.

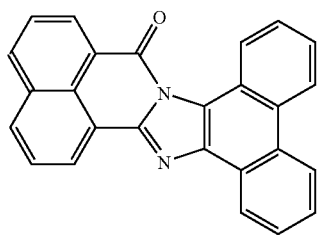

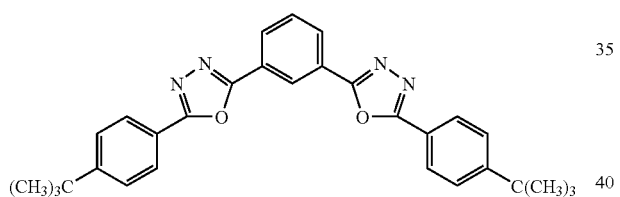

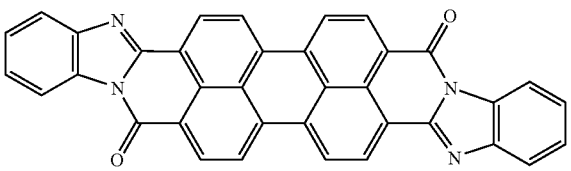

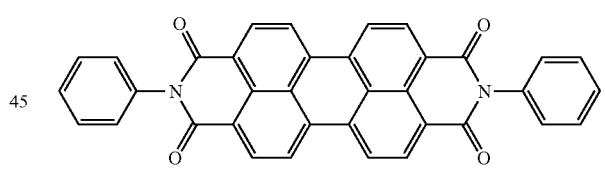

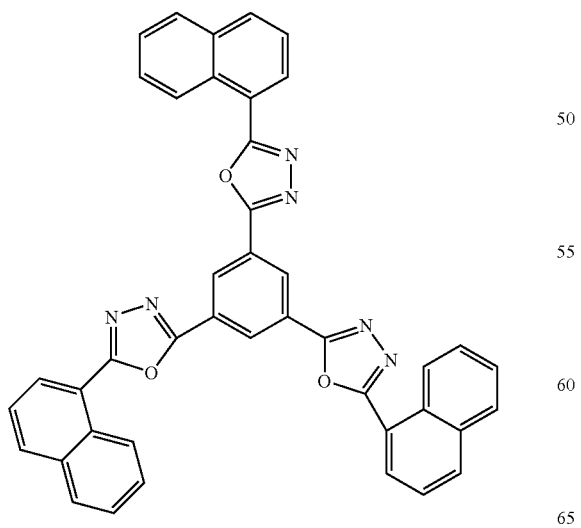

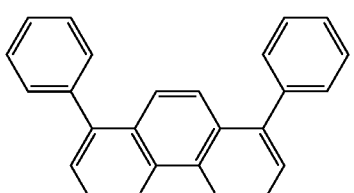
Bphen

-continued

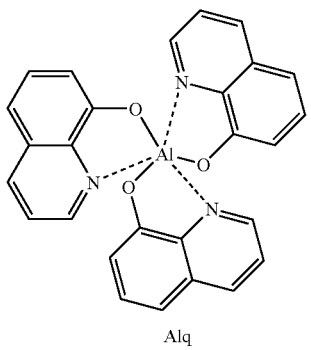

Alq

In the organic EL devices according to the present invention, each of layers containing anthryl derivative-substituted compounds represented by the general formulae (1) and (2) and layers containing other organic compounds is prepared as a thin film generally by a vacuum deposition method, an ionization deposition method, spattering, plasma, or a conventional coating method (e.g., a spin coating, dipping, casting, LB, or inkjet method) in which the compound is dissolved in an appropriate solvent. In the case of forming a film with the coating method, in particular, a film may be formed using the compound in combination with an appropriate binder resin.

The above binder resins may be chosen from a wide variety of binder resins. Examples of the binder resin include, but not limited to, polyvinyl carbazole resins, polycarbonate resins, polyester resins, polyallylate resins, polystyrene resins, ABS resins, polybutadine resins, polyurethane resins, acrylic resins, methacrylic resins, butyral resins, polyvinyl acetal resins, polyamide resins, polyimide resins, polyethylene resins, polyethersulfone resins, diallyl phthalate resins, phenol resins, epoxy resins, silicone resins, polysulfone resins, and urea resins. Each of those may also be used singly. Alternatively, two or more of them may be mixed as copolymers. Further, additives such as known plasticizers, antioxidants, and ultraviolet absorbers may be use in combination if required.

A desirable anode material has as large a work function as possible and examples of such a material include: metal elements such as gold, platinum, silver, copper, nickel, palladium, cobalt, selenium, vanadium, and tungsten, and alloys thereof; and metal oxides such as tin oxide, zinc oxide, indium oxide, indium tin oxide (ITO) and indium zinc oxide. Further, conductive polymers such as polyaniline, polypyrrole, polythiophene, and polyphenylene sulfide may also be used. Each of those electrode substances may be used singly. Alternatively, multiple of them may also be used in combination. Further, the anode may adopt any one of a single layer construction and a multilayer construction.

On the other hand, a desirable cathode material has as small a work function as possible and examples of such a material include: metal elements such as lithium, sodium, potassium, calcium, magnesium, aluminum, indium, ruthenium, titanium, manganese, yttrium, silver, lead, tin, and chromium; and multiple alloys such as lithium-indium, sodium-potassium, magnesium-silver, aluminum-lithium, aluminum-magnesium, and magnesium-indium. Metal oxides such as indium tin oxide (ITO) may also be used. Each of those electrode substances may be used singly. Alternatively, multiple of them may also be used in combination. Further, the cathode may adopt any one of a single layer construction and a multilayer construction.

In addition, at least one of the anode and cathode is desirably transparent or translucent.

Substrates which may be used in the present invention include: opaque substrates such as metallic substrates and ceramics substrates; and transparent substrates such as glass, quartz, and plastic sheet substrates, but are not particularly limited to these materials. In addition, the substrate may be a color filter film, a fluorescent color converting film, a dielectric reflection film, or the like to control colored light.

Furthermore, a protective layer or a sealing layer may be formed on the prepared device to prevent the device from contacting with oxygen, moisture, or the like. The protective layer may be a diamond thin film, a film made of an inorganic material such as metal oxide or metal nitride, a polymer film made of a fluorine resin, polyparaxylene, polyethylene, silicone resin, polystyrene resin, or the like, or may be a photo-curing resin, or the like. Furthermore, the device itself may be covered with glass, an airtight film, metal, or the like and packaged with an appropriate sealing resin.

Hereinafter, the present invention will be described more specifically with reference to examples thereof, but the invention is not limited to each of these examples.

EXAMPLE 1

Method of Manufacturing Exemplified Compound No. 20

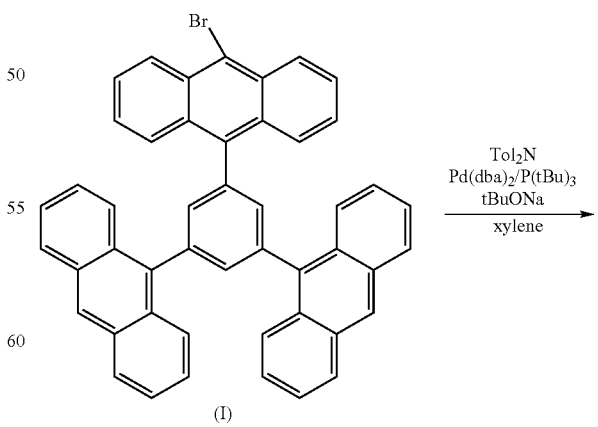

-continued

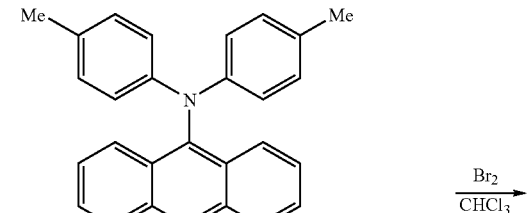

(II)

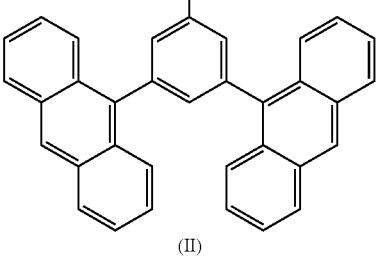

(Synthesis of Intermediate (II))

Under a nitrogen atmosphere, 458 mg (0.797 mmol) of palladium bis(benzylidene acetone) and 0.97 g (4.78 mmol) of tri-tert-butyl phosphine were dissolved in 200 ml of xylene and the mixture was stirred for 1 hour at room temperature. After 100 ml of xylene had been added to the mixture, 3.43 g (5 mmol) of Compound (I) was added to the mixture in a stream of nitrogen and the whole was stirred for 5 minutes on an oil bath heated to 50° C. Then, 1 g (5.08 mmol) of N,N-ditolylamine was dissolved in 50 ml of xylene and the solution was dropped into the mixture. Subsequently, 0.73 g (7.62 mmol) of tert-sodium butoxide was added to the mixture and the whole was heated and stirred for about 5 hours on an oil bath heated to 130° C. The temperature of the reaction solution was returned to room temperature, and then 100 ml of water was added to the solution. A water layer was separated from an organic layer in the solution and then the water layer was extracted with toluene and ethyl acetate, followed by drying the extracted layer together with the above organic layer by using sodium sulfate. The solvent was distilled off and then the remainder was purified by silica gel column chromatography (toluene: hexane=1:3), resulting in 3.01 g of Intermediate (II).

(Synthesis of Intermediate (III))

A solution of 2.5 g (3.12 mmol) of Intermediate (II) in 200 ml of chloroform was cooled to 0° C. Then, 1 g (6.25 mmol) of bromine dissolved in 50 ml of chloroform was gradually dropped into the solution. After the dropping, the mixture solution was stirred for 2 hours at room temperature and then 200 ml of methanol was added to the solution, followed by stirring the mixture for 2 hours at 5° C. A precipitate was filtrated, and then the precipitate was dispersed and washed with acetone, followed by condensing the resulting solution. Subsequently, the resulting condensate was re-cooled to 5° C. and a precipitate was filtrated, resulting in 2.7 g of Intermediate (III).

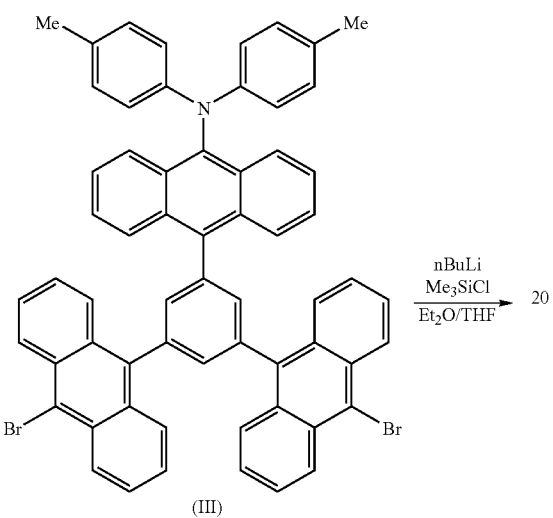

(III)

(Synthesis of Exemplified Compound No. 20)

Under a nitrogen atmosphere, a solution of 2.5 g (2.60 mmol) of Intermediate (III) in 320 ml of diethyl ether with 80 ml of THF was cooled to −78° C. Then 4 ml of n-butyl lithium (15% n-hexane solution, 6.24 mmol) was dropped into the solution and the whole was stirred for 3 hours at −78 to −40° C. The solution was cooled to −78° C. again, followed by dropping 1.13 g (10.4 mmol) of trimethylchlorosilane dissolved in 30 ml of diethyl ether into the solution. Then, the reaction solution was stirred until the temperature of the solution returned to room temperature. Subsequently, 100 ml, of water was added to the solution. A water layer was separated from an organic layer in the solution and then the water layer was extracted with diethyl ether, followed by drying the extracted layer together with the above organic layer by using sodium sulfate. The solvent was distilled off and then the remainder was purified by silica gel column chromatography (toluene:hexane=1:5), resulting in 1.2 g of Exemplified Compound No. 20.

EXAMPLE 2

Method of Manufacturing Exemplified Compounds Nos. 27 and 35

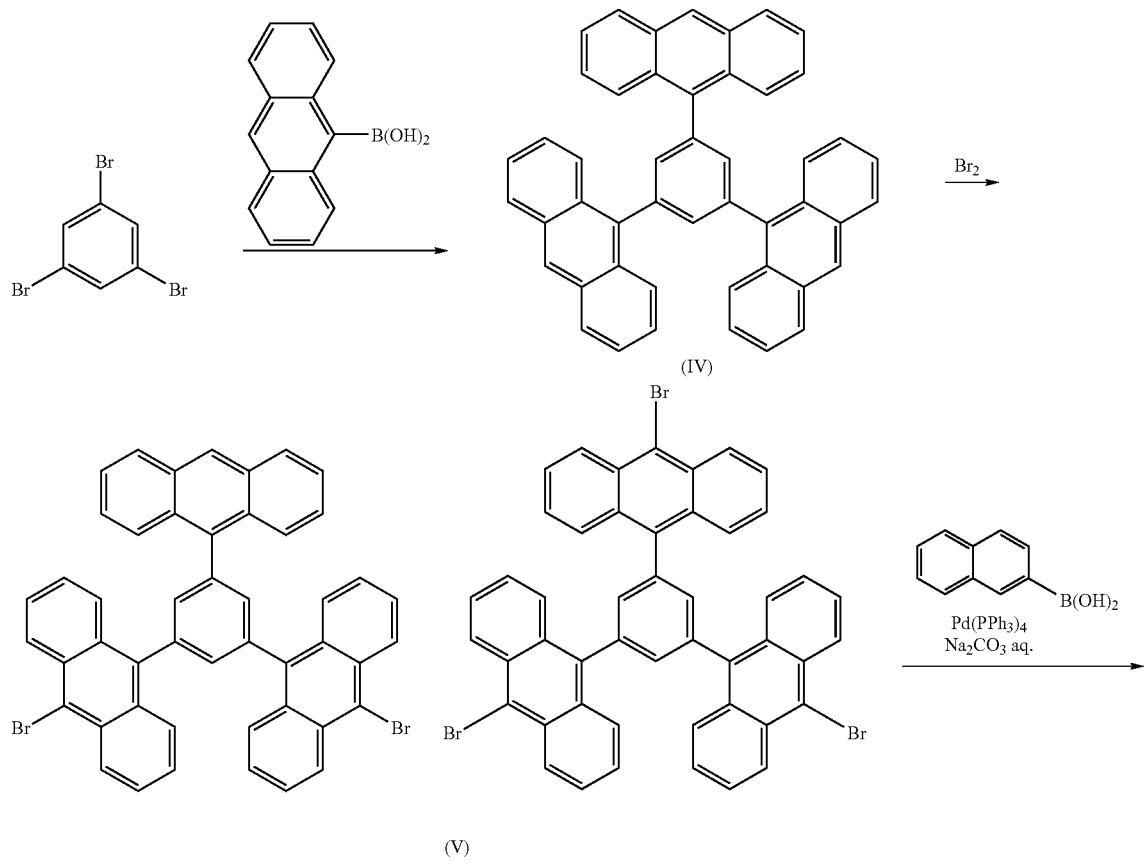

(Synthesis of Intermediate (IV))

In a stream of nitrogen, 25.8 g (82 mmol) of tribromobenzene and 109.5 g (0.491 mol) of anthracene-9-boronic acid were dissolved in a deaerated mixture solvent of 1 litter of toluene and 500 ml of ethanol and then the whole was stirred. A sodium carbonate aqueous solution prepared by dissolving 86.8 g of anhydrous sodium carbonate in 800 ml of water was dropped into the solution. In a stream of nitrogen, the resulting mixture was stirred for 1 hour on an oil bath heated to 80° C., followed by the addition of 14.2 g (12.3 mmol) of tetrakis (triphenyl phosphine) palladium. Then, the mixture was heated and stirred for about 4 hours on an oil bath heated to 80° C. The temperature of the reaction solution was returned to room temperature and further returned to 5° C., followed by filtering the precipitated crystal out. The crystal was dissolved in a mixture solvent of chlorobenzene and heptane under heat and then purified by silica gel column chromatography (chlorobenzene:heptane=1:3), resulting in 25 g of Intermediate (IV).

(Synthesis of Intermediate (V))

A solution of 16.7 g (27.6 mmol) of Intermediate (IV) in 300 ml of chloroform was cooled to 5° C. and 9.69 g (60.6 mmol) of bromine dissolved in 70 ml of chloroform was gradually dropped into the solution. After the dropping, the solution was stirred for 2 hours at room temperature. Subsequently, 300 ml of methanol was added to the solution and the whole was stirred for 2 hours at 5° C. A precipitate was filtrated, dispersed and washed with acetone, the solution was re-cooled to 5° C., and a precipitate was filtered, resulting in 21 g of Intermediate (V) as a mixture of monobromo, dibromo, and tribromo products.

(Synthesis of Exemplified Compounds Nos. 27 and 35)

In a stream of nitrogen, 5 g (6.54 mmol, in terms of the dibromo product) of Intermediate (V) and 3.37 g (19.6 mmol) of naphthalene-2-boronic acid were dissolved in a deaerated mixture solvent of 300 ml of toluene and 60 ml of ethanol and the whole was stirred, followed by dropping an aqueous solution prepared by dissolving 4.16 g of anhydrous sodium carbonate in 60 ml of water into the solution. After the mixture solution had been stirred for 30 minutes, 1.13 g (0.98 mmol) of tetrakis (triphenyl phosphine) palladium was added to the mixture solution, followed by heating and stirring the mixture on an oil bath heated to 80° C. for about 7 hours. After the temperature of the reaction solution had been returned to room temperature, 100 ml of water and 100 ml of ethyl acetate were added to the solution. A water layer was separated from an organic layer in the solution and then the water layer was extracted with toluene and ethyl acetate, followed by drying the extracted layer together with the above organic layer by using magnesium sulfate. The solvent was distilled off and then the remainder was purified by silica gel column chromatography (toluene:hexane=1:3), resulting in 1.9 g of Exemplified Compound 27 and 1 g of Exemplified Compound 35.

EXAMPLE 3

An organic EL device having the structure shown in FIG. 3 was prepared by the method described below.

On a glass substrate as a substrate 1, indium tin oxide (ITO) as an anode 2 was formed in the shape of a film with a film thickness of 120 nm by a spattering method and then used as a transparent conductive supporting substrate. Subsequently, the substrate was subjected to ultrasonic cleaning in acetone and isopropyl alcohol (IPA) in order. Next, the substrate was boiled and washed with IPA, followed by drying. Furthermore, the substrate was subjected to UV/ozone cleaning and used as a transparent conductive supporting substrate.

Using a compound represented by the following structural formula as a hole-transporting material, a chloroform solution was prepared to a concentration of 0.5 wt %.

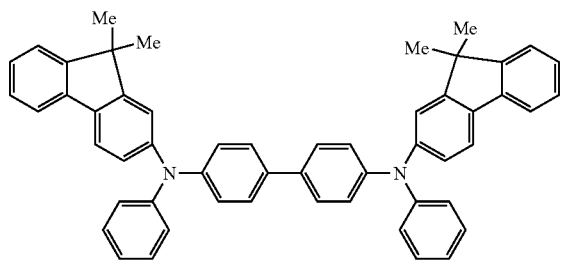

This solution was dropped onto the above ITO electrode. Subsequently, the ITO electrode was subjected to spin coating with the solution at a revolving speed of 500 rpm for 10 seconds at first and then 1,000 rpm for 1 minute to form a thin film thereon. After that, the resulting thin film was placed in a vacuum oven at 80° C. and dried for 10 minutes to completely remove the solvent in the film. Consequently, a hole-transporting layer 5 thus obtained was 50 nm in thickness. Next, for a light-emitting layer 3, Exemplified Compound No. 20 described above was deposited on the hole-transporting layer 5. The resulting light-emitting layer 3 was 20 nm in thickness. In this case, the degree of vacuum at the time of deposition was $1.0 \times 10^{-4}$ Pa and the film formation was performed at a rate of 0.2 to 0.3 nm/second.

Furthermore, bathophenanthroline (BPhen) was formed as an electron-transporting layer 6 to a thickness of 40 nm by a vacuum deposition method. In this case, the degree of vacuum at the time of deposition was $1.0 \times 10^{-4}$ Pa and the film formation was performed at a rate of 0.2 to 0.3 nm/second.

Subsequently, using an aluminum-lithium alloy (lithium conc.=1 atom %) as a deposition material, a metal layer film of 10 nm in thickness was formed on the organic layer mentioned above by a vacuum deposition method, and successively an aluminum film of 150 nm in thickness was formed thereon by a vacuum deposition method. Consequently, an organic EL device in which the aluminum-lithium alloy film was provided as an electron injection electrode (cathode 4) was prepared. In this case, the degree of vacuum at the time of deposition was $1.0 \times 10^{-4}$ Pa and the film formation was performed at a rate of 1.0 to 1.2 nm/second.

The resulting organic EL device was covered with a protective glass and sealed with an acrylic resin binder in a dry air atmosphere to prevent the device from deteriorating with the adsorption of moisture thereon.

From the device thus obtained, the inventors observed the emission of green light with a light-emitting luminance of 310 cd/m$^2$ and a luminous efficiency of 7 lm/W at an applied voltage of 3 V when the ITO electrode (anode 2) was provided as a positive electrode and the Al—Li electrode (cathode 4) was provided as a negative electrode.

Furthermore, when the current density was kept at 3.0 mA/cm$^2$ and the voltage was applied for 100 hours under a nitrogen atmosphere, the rate of luminance degradation after 100 hours was small because the luminance changed from the initial luminance of 315 cd/m$^2$ to 300 cd/m$^2$.

Compartive Example 1

An organic EL device was prepared by the same way as that of Example 4, except that the following comparative compound was used instead of Exemplified Compound No. 20, followed by subjecting the device to the same evaluation. The inventors observed the emission of green light with a light-emitting luminance of 190 cd/m$^2$ and a luminous efficiency of 2 lm/W at an applied voltage of 3 V.

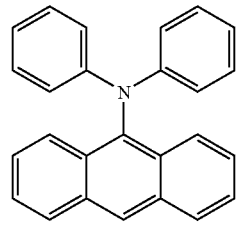

Furthermore, when the current density was kept at 3.0 mA/cm$^2$ and a voltage was applied for 100 hours under a nitrogen atmosphere, the rate of luminance degradation after 100 hours was large because the luminance changed from the initial luminance of 180 cd/m$^2$ to 80 cd/m$^2$.

EXAMPLES 4 TO 6

Organic EL devices were prepared by the same way as that of Example 3, except that the compounds listed in Table 1 were used instead of Exemplified Compound No. 15, followed by subjecting the devices to the same evaluation. The results were shown in Table 1.

TABLE 1

| Example | Exemplified Compound No. | Applied voltage (V) | Luminance (cd/m$^2$) | Efficiency (lm/W) |
| --- | --- | --- | --- | --- |
| 4 | 6 | 3 | 315 | 6 |
| 5 | 27 | 3 | 245 | 4 |
| 6 | 31 | 3 | 280 | 5 |

EXAMPLE 7

An organic EL device having the structure shown in FIG. 3 was prepared by the same way as that of Example 3, except that 2,9-bis [2-(9,9-dimethylfluorenyl)] phenanthroline was used in an electron-transporting layer 6 and Exemplified Compound No. 19 described above was deposited as a light-emitting layer 3.

From the device thus obtained, the inventors observed the emission of green light with a light-emitting luminance of 330 cd/m$^2$ and a luminous efficiency of 8 lm/W at an applied voltage of 3 V when the ITO electrode (anode 2) was provided as a positive electrode and the Al—Li electrode (cathode 4) was provided as a negative electrode.

EXAMPLE 8

An organic EL device was prepared by the same way as that of Example 7, except that Exemplified Compound No. 35 described above was deposited as a light-emitting layer 3.

From the device thus obtained, the inventors observed the emission of blue light with a light-emitting luminance of 260 cd/m$^2$ and a luminous efficiency of 4.5 lm/W at an applied voltage of 3 V when the ITO electrode (anode 2) was provided as a positive electrode and the Al—Li electrode (cathode 4) was provided as a negative electrode.

EXAMPLES 9 TO 16

Just as in the case of Example 8, organic EL devices were prepared by the same way as that of Example 7, except that the compounds listed in Table 2 were used, followed by subjecting the devices to the same evaluation. The results were shown in Table 2.

TABLE 2

| Example | Exemplified Compound No. | Applied voltage (V) | Luminance (cd/m$^2$) | Efficiency (lm/W) |
|---|---|---|---|---|
| 9  | 7  | 3 | 290 | 5 |
| 10 | 20 | 3 | 320 | 6 |
| 11 | 25 | 3 | 340 | 6.5 |
| 12 | 32 | 3 | 305 | 6 |
| 13 | 36 | 3 | 270 | 5 |

EXAMPLE 14

An organic EL device having the structure shown in FIG. 3 was prepared by the same way as that of Example 7, except that Exemplified Compounds Nos. 7 and 35 were co-deposited (weight ratio=15:100) as a light-emitting layer 3.

From the device thus obtained, the inventors observed the emission of green light with a light-emitting luminance of 310 cd/m and a luminous efficiency of 7 lm/W at an applied voltage of 3 V when the ITO electrode (anode 2) was provided as a positive electrode and the Al—Li electrode (cathode 4) was provided as a negative electrode.

EXAMPLE 15

A voltage was applied to the organic EL device prepared in Example 10 for 10 hours while the current density was kept at 3.0 mA/cm$^2$ under a nitrogen atmosphere. Consequently, the rate of luminance degradation after 100 hours was small because the luminance changed from the initial luminance of 325 cd/m$^2$ to 300 cd/m$^2$.

EXAMPLE 16

A voltage was applied to the organic EL device prepared in Example 11 for 10 hours while the current density was kept at 3.0 mA/cm$^2$ under a nitrogen atmosphere. Consequently, the rate of luminance degradation after 100 hours was small because the luminance changed from the initial luminance of 335 cd/m$^2$ to 320 cd/m$^2$.

Comparative Example 2

An organic EL device was prepared by the same way as that of Example 7, except that the following unsubstituted comparative compound was used in a light-emitting layer 3.

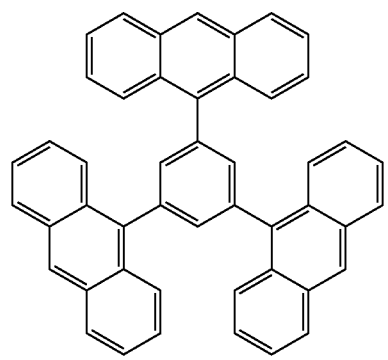

From the device thus obtained, the inventors observed the emission of light with a light-emitting luminance of 240 cd/m$^2$ and a luminous efficiency of 0.2 lm/W at an applied voltage of 6 V when the ITO electrode 2 was provided as a positive electrode and the Al—Li electrode 4 was provided as a negative electrode.

From the above description with the embodiments and examples of the present invention, the substituted anthryl derivatives of the present invention represented by the general formula (1) and by the general formula (1) in which $X_1$ is represented by the general formula (2) or (3) were developed on the basis of the design index as described in the summary of the invention. Thus, the organic EL device using the materials of the invention allowed high-efficient emission of light at a lower applied voltage. In addition, various luminescent colors can be easily obtained by replacing the substituent from one to another and excellent durability can be also attained.

What is claimed is:

1. A substituted anthryl derivative represented by the following general formula (1):

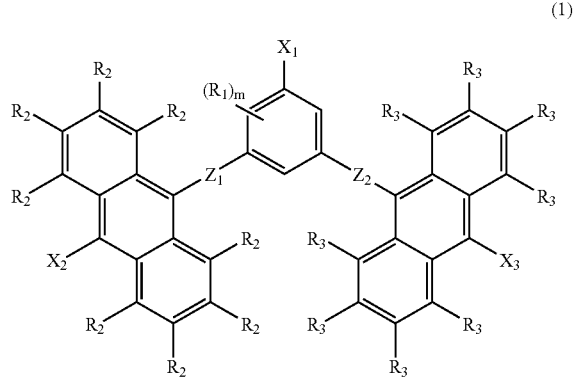

(1)

wherein $X_1$ is represented by the following general formula (3):

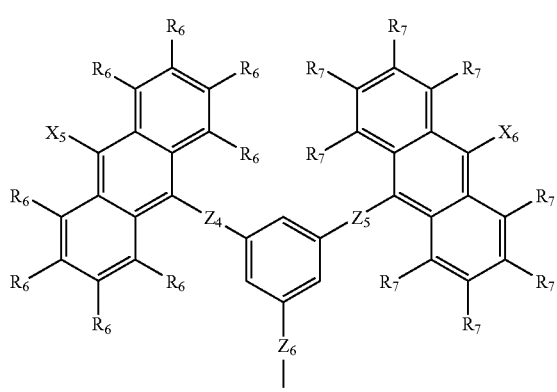

(3)

wherein each of $X_5$ and $X_6$ is one selected from the group consisting of a heavy hydrogen atom, a halogen atom, a substituted or unsubstituted alkyl group, alkenyl group, alkynyl group, aralkyl group, alkoxy group, and sulfide group, aryl groups including a substituted phenyl group, substituted or unsubstituted biphenyl group, terphenyl group, naphthyl group, phenanthryl group, pyrenyl group, tetracenyl group, and perylenyl group, a substituted or unsubstituted heterocyclic group, and a substituted silyl group, and $X_5$ and $X_6$ may be the same or different;

each of $Z_4$ and $Z_5$ is one selected from the group consisting of a direct bond, a substituted or unsubstituted alkylene group, alkenylene group, alkynylene group, aralkylene group, arylene group, and divalent heterocyclic group, and a divalent substituent having a coupling group, and $Z_4$ and $Z_5$ may be the same or different;

$Z_6$ is one selected from the group consisting of a direct bond, a substituted or unsubstituted alkylene group, alkenylene group, alkynylene group, and aralkylene group, arylene groups selected from a substituted or unsubstituted phenylene group, biphenylene group, terphenylene group, naphthylene group, fluorenylene group, phenanthrylene group, pyrenylene group, tetracenylene group, pentacenylene group, and perylenylene group, a substituted or unsubstituted divalent heterocyclic group, and a divalent substitutent having a coupling group, and $Z_6$ may be the same or different;

each of $R_6$ and $R_7$ is one selected from the group consisting of a hydrogen atom, a heavy hydrogen atom, a halogen atom, a substituted or unsubstituted alkyl group, aryl group, alkoxy group, and amino group, and $R_6$ and $R_7$ may be the same or different; and n is an integer of 0 to 3:

each of $X_2$ and $X_3$ is one selected from the group consisting of a heavy hydrogen atom, a substituted or unsubstituted alkyl group, alkenyl group, alkynyl group, aralkyl group, alkoxy group, and sulfide group, aryl groups including a substituted phenyl group, a substituted or unsubstituted terphenyl group, naphthyl group, phenanthryl group, pyrenyl group, tetracenyl group, and perylenyl group, a substituted or unsubstituted heterocyclic group, and a substituted silyl group, $X_2$ and $X_3$ may be the same or different, and, when $X_1$ is not an aryl group having an amino group, one of $X_2$ and $X_3$ may be a substituted or unsubstituted amino group, or a substituted or unsubstituted amino group having a coupling group;

each of $Z_1$ and $Z_2$ is one selected from the group consisting of a direct bond, a substituted or unsubstituted alkylene group, alkenylene group, alkynylene group, aralkylene group, arylene group, and divalent heterocyclic group, and a divalent substitutent having a coupling group, and $Z_1$ and $Z_2$ may be the same or different;

$R_1$ is one selected from the group consisting of a hydrogen atom, a heavy hydrogen atom, a halogen atom, a substituted or unsubstituted alkyl group, and alkoxy group, and $R_1$ may be the same or different;

each of $R_2$ and $R_3$ is one selected from the group consisting of a hydrogen atom, a heavy hydrogen atom, a halogen atom, a substituted or unsubstituted alkyl group, aryl group, alkoxy group, and amino group, and $R_2$ and $R_3$ may be the same or different; and m is an integer of 0 to 3.

* * * * *

UNITED STATES PATENT AND TRADEMARK OFFICE
CERTIFICATE OF CORRECTION

PATENT NO. : 7,129,386 B2
APPLICATION NO. : 10/875244
DATED : October 31, 2006
INVENTOR(S) : Akihito Saitoh et al.

It is certified that error appears in the above-identified patent and that said Letters Patent is hereby corrected as shown below:

COLUMN 25:

Compound 26, " " should read -- --.

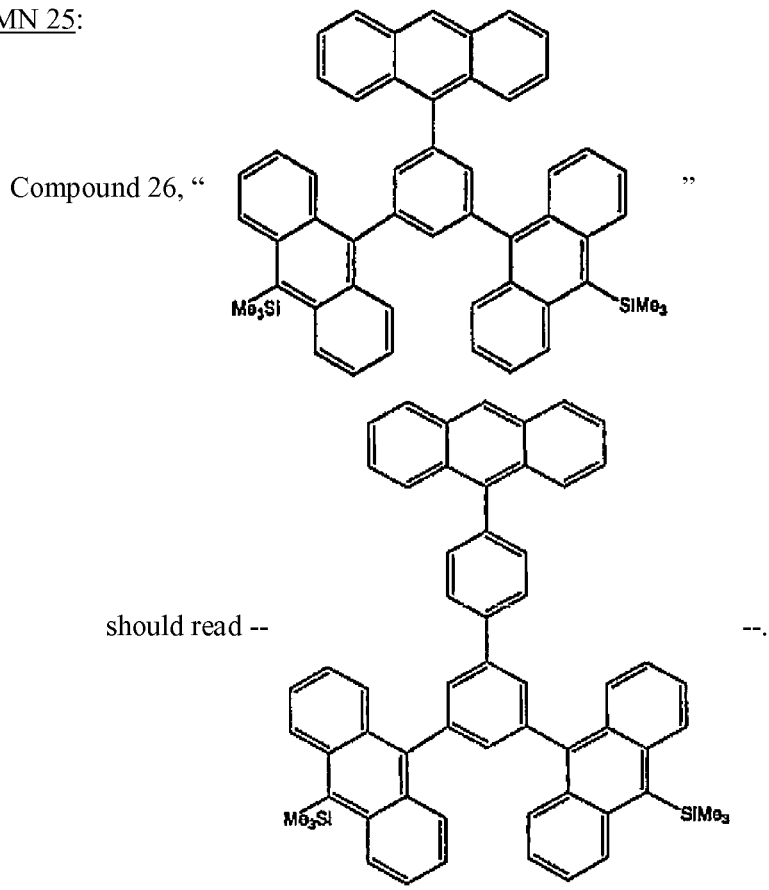

COLUMN 40:

Lines 31-33, " Pc-M M: Cu, Mg, AlCl, MnCl, GaCl, etc. " should read -- Pc-M M: Cu, Mg, AlCl, TiO, SiCl$_2$, Zn, Sn, MnCl, GaCl, etc. --.

COLUMN 54:

Line 30, " Pd(PPh$_3$)$_4$ / Na$_2$CO$_3$ aq. → " should read -- Pd(PPh$_3$)$_4$ / Na$_2$CO$_3$ aq. / toluene/EtOH → --; and Line 40, "24.35" should read --27.35--.

UNITED STATES PATENT AND TRADEMARK OFFICE
CERTIFICATE OF CORRECTION

PATENT NO.         : 7,129,386 B2                              Page 2 of 2
APPLICATION NO.    : 10/875244
DATED              : October 31, 2006
INVENTOR(S)        : Akihito Saitoh et al.

It is certified that error appears in the above-identified patent and that said Letters Patent is hereby corrected as shown below:

<u>COLUMN 60</u>:

Line 11, "3:" should read --3;--.

Signed and Sealed this

Thirty-first Day of July, 2007

JON W. DUDAS
*Director of the United States Patent and Trademark Office*